US012678083B2

(12) United States Patent
Yeo et al.

(10) Patent No.: US 12,678,083 B2
(45) Date of Patent: Jul. 14, 2026

(54) MULTIFUNCTIONAL BIOPATCH FOR WIRELESS MONITORING OF HEALTH CONDITIONS AND METHODS THEREOF

(71) Applicants: Georgia Tech Research Corporation, Atlanta, GA (US); Emory University, Atlanta, GA (US); Children's Healthcare of Atlanta, Atlanta, GA (US)

(72) Inventors: Woon-Hong Yeo, Atlanta, GA (US); Kevin O. Maher, Atlanta, GA (US)

(73) Assignees: Georgia Tech Research Corporation, Atlanta, GA (US); Emory University, Atlanta, GA (US); Children's Healthcare of Atlanta, Atlanta, GA (US)

( * ) Notice: Subject to any disclaimer, the term of this patent is extended or adjusted under 35 U.S.C. 154(b) by 974 days.

(21) Appl. No.: 16/972,714

(22) PCT Filed: Jun. 7, 2019

(86) PCT No.: PCT/US2019/036043
§ 371 (c)(1),
(2) Date: Dec. 7, 2020

(87) PCT Pub. No.: WO2019/236993
PCT Pub. Date: Dec. 12, 2019

(65) Prior Publication Data
US 2021/0259606 A1 Aug. 26, 2021

Related U.S. Application Data

(60) Provisional application No. 62/835,098, filed on Apr. 17, 2019, provisional application No. 62/682,312, filed on Jun. 8, 2018.

(51) Int. Cl.
A61B 5/00 (2006.01)
A61B 5/28 (2021.01)
H05K 1/02 (2006.01)

(52) U.S. Cl.
CPC .............. *A61B 5/28* (2021.01); *A61B 5/0004* (2013.01); *A61B 5/0015* (2013.01);
(Continued)

(58) Field of Classification Search
CPC ....... A61B 5/28; A61B 5/0004; A61B 5/0015; A61B 5/7264; A61B 5/6833;
(Continued)

(56) References Cited

U.S. PATENT DOCUMENTS 8,552,299 B2 10/2013 Rogers et al.
2013/0041235 A1* 2/2013 Rogers ..................... A61N 1/05
600/386

(Continued)

FOREIGN PATENT DOCUMENTS

WO 2017/164902 9/2017

OTHER PUBLICATIONS

F. Fondjo, D. S. Lee, C. Howe, W.-H. Yeo and J.-H. Kim, "Synthesis of a Soft Nanocomposite for Flexible, Wearable Bioelectronics," 2017 IEEE 67th Electronic Components and Technology Conference (ECTC), Orlando, FL, USA, 2017, pp. 780-785, doi: 10.1109/ECTC.2017.195. (Year: 2017).*

(Continued)

*Primary Examiner* — Joanne M Rodden
*Assistant Examiner* — Dana Stumpfoll
(74) *Attorney, Agent, or Firm* — TROUTMAN PEPPER LOCKE LLP; Ryan A. Schneider; Stephanie J. Remy

(57) ABSTRACT

Stretchable condition-monitoring biopatch devices are disclosed. The stretchable condition-monitoring biopatches may include an elastomer layer. The elastomer layer may (Continued)

adhere to the skin without use of an adhesive. The devices described herein may include stretchable electrodes configured to sense physiological potentials from the patient or subject. The device may include a stretchable circuit board. The stretchable electrodes may be in electrical communication with the stretchable circuit board via stretchable circuits. Methods for providing machine-learning neural networks are disclosed. These methods may include convolution neural networks that incorporate inception-type convolution units that may classify and diagnose conditions based on signals detected by the condition-monitoring biopatches.

19 Claims, 20 Drawing Sheets

(52) U.S. Cl.
CPC .......... *A61B 5/7264* (2013.01); *A61B 5/6833* (2013.01); *A61B 2562/0209* (2013.01); *A61B 2562/0219* (2013.01); *A61B 2562/028* (2013.01); *A61B 2562/125* (2013.01); *A61B 2562/164* (2013.01); *A61B 2562/166* (2013.01); *H05K 1/0283* (2013.01); *H05K 2201/0133* (2013.01)

(58) Field of Classification Search
CPC ...... A61B 2562/0209; A61B 2562/028; A61B 2562/125; A61B 2562/164; A61B 2562/166; A61B 5/282; A61B 2562/0219; A61B 5/259; H05K 1/0283; H05K 2201/0133; H05K 1/0243; H05K 3/284; H05K 1/0277; H05K 1/028; H05K 1/118; H05K 1/189; H05K 2201/09263; H05K 1/0272; H05K 2201/0195
See application file for complete search history.

(56) References Cited

U.S. PATENT DOCUMENTS

| | | | | |
|---|---|---|---|---|
| 2014/0358197 | A1* | 12/2014 | Mashiach | A61B 5/0031 607/60 |
| 2019/0272920 | A1* | 9/2019 | Teplitzky | G06N 3/045 |
| 2019/0365263 | A1* | 12/2019 | Raj | A61B 5/0024 |

OTHER PUBLICATIONS

Romeo, Alessia, Qihan Liu, Zhigang Suo, and Stephanie P. Lacour. 2013. "Elastomeric Substrates with Embedded Stiff Platforms for Stretchable Electronics." Applied Physics Letters 102 (13): 131904. https://doi.org/10.1063/1.4799653. (Year: 2013).*

Jang, et al., "Rugged and Breathable Forms of Stretchable Electronics with Adherent Composite Substrates for Transcutaneous Monitoring," Nature Communications, vol. 5, Sep. 3, 2014 (Year: 2014).*

Sheng Xu et al., Soft Microfluidic Assemblies of Sensors, Circuits, and Radios for the Skin. Science344,70-74(2014).DOI:10.1126/science.1250169 (Year: 2014).*

Liu, Li, et al. "Silicone-based adhesives for long-term skin application" Biomedical Physics & Engineering Express, IOP Publishing, Sep. 10, 2017, iopscience.iop.org/article/10.1088/2057-1976/aa91fb. (Year: 2017).*

Sterken, et al., "Ultra_Thin Chip package (UTCP) and Stretchable Circuit Technologies for Wearable ECG System," Conf Proc IEEE Eng Med Biol Soc., 2011 (Year: 2011).*

International Search Report and Written Opinion from Application No. PCT/US2019/036043 dated Oct. 2, 2019 (13 pages).

Sterken, et al., "Ultra_Thin Chip package (UTCP) and Stretchable Circuit Technologies for Wearable ECG System," Conf Proc IEEE Eng Med Biol Soc., 2011.

Jang, et al., "Rugged and Breathable Forms of Stretchable Electronics with Adherent Composite Substrates for Transcutaneous Monitoring," Nature Communications, vol. 5, Sep. 3, 2014.

* cited by examiner

112

102b

208

202

206

204

102a

1000

MULTIFUNCTIONAL BIOPATCH FOR WIRELESS MONITORING OF HEALTH CONDITIONS AND METHODS THEREOF

CROSS-REFERENCE TO RELATED APPLICATIONS

This application claims priority, and benefit under 35 U.S.C. § 119 (e), to U.S. Provisional Patent Application No. 62/682,312, filed 8 Jun. 2018, and to U.S. Provisional Patent Application No. 62/835,098, filed 17 Apr. 2019. The disclosures of these prior applications are hereby incorporated by reference as if fully set forth below.

FIELD OF THE DISCLOSURE

Embodiments of the present disclosure relate to stretchable biopatches and, more particularly, to stretchable biopatches that monitor health conditions and provide wireless connectivity.

BACKGROUND

Monitoring the electrocardiogram (ECG) is of great interest to both health care providers and patients alike since it manifests the heart's condition with a straightforward device setup. Many cardiac abnormalities, such as myocardial ischemia/infarction and several types of arrhythmia can be detected by inspecting the waveforms collected by ECG. ECG also provides clinicians a range of indirect measures of the patient's condition, including but not limited to prognostic estimation, postoperative recovery, drug efficacy, mental stress, and risk of sudden cardiac death.

For the latter type of investigations, health care providers may need to assess the heart for extended periods and evaluate the trends in long-term cardiac activities to make appropriate clinical decisions. In these scenarios, the standard method for diagnosis is a Holter monitor, a portable ECG device that includes a hardware component that has wired leads that attach to the body. The Holter monitor can be strapped to the patient for a 24-hour ambulatory ECG recording. Despite its value in the acquisition of long-term ECG data, Holter monitors have various limitations that limit their utility as a biomedical device. For example, the data acquisition unit, bundles of cables, gelled adhesive electrodes, tapes, and straps all work to disrupt daily activities and sleep. The signals recorded by the device are reviewed by the doctor retrospectively, making it difficult to perform timely interventions. The gels used in the setup can dry over time and degrade the ECG signals, and the gels can also cause skin irritation.

Hospital-based systems for monitoring health conditions pose similar problems, as hospitals continue to use lab-based, rigid, bulky machines that also include gelled adhesive electrodes. In the context of neonatal intensive care units (NICU), these bulky machines are far from ideal for the small patients, as tiny infants can hardly articulate pain and uncomfortableness. Additionally, the gel-based electrodes are much more troublesome for newborn skin.

What is needed is a system that eliminates the bulky, bundle-of-wires approach of present systems. Ideally, a system would provide an ultrathin, comfortable, stretchable biopatch that allows wireless monitoring of the patient or subject.

SUMMARY

Embodiments of the present disclosure address these concerns as well as other needs that will become apparent upon reading the description below in conjunction with the drawings. Briefly described, embodiments of the present disclosure relate to stretchable biopatches and, more particularly, to stretchable biopatches that monitor health conditions and provide wireless connectivity.

An exemplary embodiment of the present invention provides a condition-monitoring device. The device can include an elastomer layer comprising a first side and a second side. The device can include a first electrode positioned proximate the first side of the elastomer and extending at least partially from the elastomer layer to a position outside of the elastomer layer. The first electrode can be configured to sense physiological potentials from a person and produce a voltage. The device can include a stretchable circuit board disposed at least partially within the elastomer layer and in electrical communication with the first electrode. The device can include a microcontroller electrically connected to the stretchable circuit board and in electrical communication with the first electrode. The device may include a first stretchable circuit providing electrical communication between the first electrode and the stretchable circuit board. The first stretchable circuit can be configured to stretch with the elastomer layer. The microcontroller can receive the voltage from the first electrode via the first stretchable circuit.

In any of the embodiments described herein, the stretchable circuit board can be positioned proximate the second side of the elastomer layer. The stretchable circuit board and the microcontroller can be encapsulated within the elastomer layer.

In any of the embodiments described herein, the elastomer layer can be configured to adhere to a layer of skin without an adhesive via a natural adhesion of the elastomer layer.

In any of the embodiments described herein, the device can include a second electrode positioned proximate the first side of the elastomer layer and extending at least partially from the elastomer layer to a position outside of the elastomer layer. The device can include a second stretchable circuit connecting the second electrode to the stretchable circuit board. The second stretchable circuit can be configured to stretch with the elastomer layer.

In any of the embodiments described herein, the device can include a fluid layer disposed within the elastomer layer and between the first side of the elastomer layer and the stretchable circuit board.

In any of the embodiments described herein, a work of adhesion value for the elastomer layer can be greater than 0.25 N/m.

In any of the embodiments described herein, a work of adhesion value for the elastomer layer can be greater than 0.50 N/m.

In any of the embodiments described herein, a thickness of the elastomer layer can be from 200 μm to 2 mm.

In any of the embodiments described herein, the device can include a microelectromechanical system (MEMS) device in electrical communication with the microcontroller. The MEMS device can include at least one of an accelerometer, a gyroscope, or a thermistor.

In any of the embodiments described herein, the MEMS device can be disposed on the stretchable circuit board. The stretchable circuit board can be positioned proximate the second side of the elastomer layer. The stretchable circuit board, the microcontroller, and the MEMS device can be encapsulated within the elastomer layer.

In any of the embodiments described herein, the device can include an antenna. The antenna can be configured to transmit a wireless signal from the microcontroller to a computing device. The wireless signal can include data associated with the phycological potentials.

Another exemplary embodiment of the present invention provides a condition-monitoring device. The device can include an elastomer layer comprising a first side and a second side. The device can include a positive electrode comprising a first plurality of electrode units. The first plurality of electrode units can be positioned proximate the first side of the elastomer layer. The positive electrode can be configured to sense physiological potentials from a person and produce a first voltage. The device can include a first plurality of stretchable circuits in electrical communication with the first plurality of electrode units. The device can include a negative electrode comprising a second plurality of electrode units. The second plurality of electrode units can be positioned proximate the first side of the elastomer layer. The negative electrode can be configured to sense the physiological potentials from the person and produce a second voltage. The device can include a second plurality of stretchable circuits in electrical communication with the second plurality of electrode units. The device can include a stretchable circuit board disposed at least partially within the elastomer layer and in electrical communication with the positive and negative electrodes. The device can include a microcontroller electrically connected to the stretchable circuit board and in electrical communication with the positive and negative electrodes. The device can include a third stretchable circuit providing electrical communication between the positive electrode and the stretchable circuit board. The microcontroller can receive the first voltage from the positive electrode via the third stretchable circuit. The device can include a fourth stretchable circuit providing electrical communication between the negative electrode and the stretchable circuit board. The microcontroller can receive the second voltage from the negative electrode via the fourth stretchable circuit. The first, second, third, and fourth stretchable circuits can be configured to stretch with the elastomer layer.

In any of the embodiments described herein, the stretchable circuit board can be positioned proximate the second side of the elastomer layer. The stretchable circuit board and the microcontroller can be encapsulated within the elastomer layer.

In any of the embodiments described herein, the elastomer layer can be configured to adhere to a layer of skin without an adhesive.

In any of the embodiments described herein, the device can include a fluid layer disposed within the elastomer layer and between the first side of the elastomer layer and the stretchable circuit board.

In any of the embodiments described herein, a work of adhesion value for the elastomer layer can be greater than 0.25 N/m.

In any of the embodiments described herein, a work of adhesion value for the elastomer layer can be greater than 0.50 N/m.

In any of the embodiments described herein, a thickness of the elastomer layer can be from 200 μm to 2 mm.

In any of the embodiments described herein, the device can include a microelectromechanical system (MEMS) device in electrical communication with the microcontroller. The MEMS device can include at least one of an accelerometer, a gyroscope, or a thermistor.

In any of the embodiments described herein, the MEMS device can be disposed on the stretchable circuit board. The stretchable circuit board can be positioned proximate the second side of the elastomer layer. The stretchable circuit board, the microcontroller, and the MEMS device can be encapsulated within the elastomer layer.

In any of the embodiments described herein, the device can include an antenna. The antenna can be configured to transmit a wireless signal from the microcontroller to a computing device. The wireless signal can include data associated with the phycological potentials.

Another exemplary embodiment of the present invention provides a method. The method can include placing an electrode patch on a skin of a patient. The electrode patch can include an elastomer layer comprising a first side and a second side, wherein the first side is proximate the skin. The electrode patch can include a first electrode positioned proximate the first side of the elastomer layer and at least partially in contact with the skin. The first electrode can be configured to sense physiological potentials from the patient and produce a voltage. The electrode patch can include a stretchable circuit board disposed at least partially within the elastomer layer and in electrical communication with the first electrode. The electrode patch can include a microcontroller electrically connected to the stretchable circuit board and in electrical communication with the first electrode. The electrode patch can include a first stretchable circuit providing electrical communication between the first electrode and the stretchable circuit board. The first stretchable circuit can be configured to stretch with the elastomer layer, and the microcontroller can receive the voltage from the first electrode via the first stretchable circuit. The method can include receiving, at a computing device, an output signal from the microcontroller. The output signal can include data associated with the physiological potentials. The method can include monitoring the output signal via the computing device.

In any of the embodiments described herein, the stretchable circuit board can be positioned proximate the second side of the elastomer layer. The stretchable circuit board and the microcontroller can be encapsulated within the elastomer layer.

In any of the embodiments described herein, the elastomer layer can be configured to adhere to the skin without an adhesive.

In any of the embodiments described herein, the electrode patch can include a second electrode positioned proximate the first side of the elastomer layer and in contact with the skin. The electrode patch can include a second stretchable circuit connecting the second electrode to the stretchable circuit board. The second stretchable circuit can be configured to stretch with the elastomer layer.

In any of the embodiments described herein, the electrode patch can include a fluid layer disposed within the elastomer layer.

In any of the embodiments described herein, a work of adhesion value for the elastomer layer can be greater than 0.25 N/m.

In any of the embodiments described herein, a work of adhesion value for the elastomer layer can be greater than 0.50 N/m.

In any of the embodiments described herein, a thickness of the elastomer layer can be from 200 μm to 2 mm.

In any of the embodiments described herein, the electrode patch can include a microelectromechanical system (MEMS) device. The MEMS device can include at least one of an accelerometer, a gyroscope, or a thermistor. The output signal can include data associated with a signal produced by the MEMS device.

In any of the embodiments described herein, the MEMS device can be disposed on the stretchable circuit board. The stretchable circuit board can be positioned proximate the second side of the elastomer layer. The stretchable circuit board, the microcontroller, and the MEMS device can be encapsulated within the elastomer layer.

In any of the embodiments described herein, the electrode patch can include an antenna configured to wirelessly transmit the output signal to the computing device.

In any of the embodiments described herein, the method can include receiving, at the computing device, labeled input data comprising physiological input data and diagnosis output data. The method can include applying, using the computing device, a convolution neural network model to the labeled input data to generate a first set of rules associated with the physiological input data and the diagnosis output data. The method can include applying, using the computing device, the convolution neural network model to the output signal to generate a second set of rules associated with the output signal. The method can include calculating, using the computing device, a diagnosis based on a comparison of the first set of rules and the second set of rules.

In any of the embodiments described herein, the method can include receiving, at the computing device, labeled input data comprising movement input data and diagnosis output data. The method can include applying, using the computing device, a convolution neural network model to the labeled input data to generate a first set of rules associated with the movement input data and the diagnosis output data. The method can include applying, using the computing device, the convolution neural network model to the output signal to generate a second set of rules associated with the output signal. The method can include calculating, using the computing device, a diagnosis based on a comparison of the first set of rules and the second set of rules.

Another exemplary embodiment of the present invention provides a system. The system can include one or more processors. The system can include a memory in communication with the one or more processors. The memory can store instructions that, when executed by the one or more processors, can cause the system to receive a first plurality of physiological data. The instructions can cause the system to identify one or more electrocardiogram (ECG) recordings in the first plurality of physiological data. The instructions can cause the system to identify one or more diagnoses in the first plurality of physiological data. The instructions can cause the system to train a convolution neural network model based on the identified one or more ECG recordings and the diagnoses. The instructions can cause the system to generate, using the convolution neural network model, a first set of rules associated with the first plurality of physiological data. The instructions can cause the system to receive, from an electrode patch comprising a stretchable elastomer layer and a plurality of stretchable electrodes, an electrode signal. The instructions can cause the system to generate, using the convolution neural network model, a second set of rules associated with the electrode signal. The instructions can cause the system to calculate a diagnosis based on a comparison of the first set of rules and the second set of rules.

In any of the embodiments described herein, the first plurality of physiological data can be associated with a diagnostic database.

In any of the embodiments described herein, the first plurality of physiological data can be associated with a clinical trial.

In any of the embodiments described herein, the memory can store instructions that, when executed by the one or more processors, can cause the system to receive a second plurality of physiological data. The instructions can cause the system to re-train the convolution neural network model based on the second plurality of physiological data.

In any of the embodiments described herein, the electrode signal can be received via a wireless connection with the electrode patch.

Another exemplary embodiment of the present invention provides a method. The method can include preparing a stretchable electrode. Preparing the stretchable electrode can include coating a first silicon wafer with polydimethylsiloxane (PDMS) to create a first donor substrate. Preparing the stretchable electrode can include coating the first donor substrate with a first polyimide layer. Preparing the stretchable electrode can include depositing a layer of chromium. Preparing the stretchable electrode can include depositing a layer of gold. Preparing the stretchable electrode can include patterning an electrode design on the first donor substrate via photolithography. Preparing the stretchable electrode can include coating the first donor substrate with a second polyimide layer. Preparing the stretchable electrode can include etching the second polyimide layer to expose the electrode design. Preparing the stretchable electrode can include removing the stretchable electrode from the first donor substrate. The method can include preparing a stretchable circuit board. Preparing the stretchable circuit board can include coating a second silicon wafer with PDMS to create a second donor substrate. Preparing the stretchable circuit board can include coating the second donor substrate with a third polyimide layer. Preparing the stretchable circuit board can include depositing a first layer of conductive material. Preparing the stretchable circuit board can include patterning a circuit design on the second donor substrate via photolithography. Preparing the stretchable circuit board can include coating the second donor substrate with a fourth polyimide layer. Preparing the stretchable circuit board can include etching the fourth polyimide layer via reactive ion etching. Preparing the stretchable circuit board can include depositing a second layer of conductive material. Preparing the stretchable circuit board can include coating the second donor substrate with a fifth polyimide layer. Preparing the stretchable circuit board can include exposing the circuit design by patterning the fifth polyimide layer via photolithography. Preparing the stretchable circuit board can include removing the stretchable circuit board from the second donor substrate. The method can include transferring the stretchable electrode and the stretchable circuit board to an elastomer.

In any of the embodiments described herein, the method can include encapsulating the stretchable circuit board within the elastomer.

In any of the embodiments described herein, the layer of gold, the layer of chromium, the first layer of conductive material, and the second layer of conductive material can be deposited via sputtering.

In any of the embodiments described herein, the first and second layer of conductive material can include copper.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE DRAWINGS

Reference will now be made to the accompanying figures and diagrams, which are not necessarily drawn to scale, and wherein.

DETAILED DESCRIPTION

Figure 1:
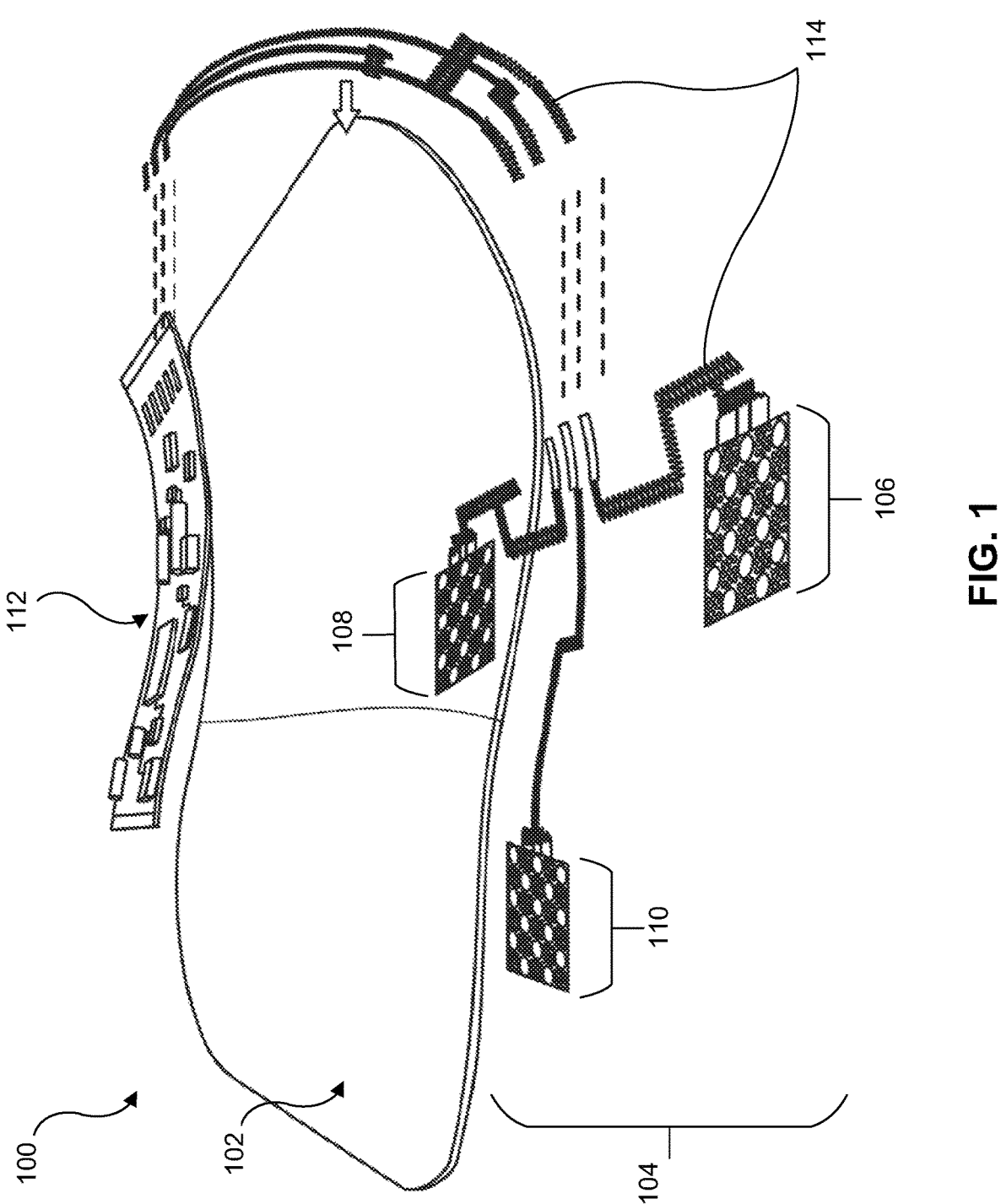
FIG. 1 is a perspective view of an exemplary monitoring device, according to some embodiments of the present disclosure.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

As used in this application, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of stretchable biopatches that monitor health conditions and provide wireless connectivity. The present disclosure, however, is not so limited and can be applicable in other contexts. For example, and not limitation, the systems and methods described herein may improve health- and condition-monitoring in other devices outside of the context of stretchable biopatches. This may include incorporating the systems or methods into traditional, inelastic electrode devices. Additionally, certain systems and methods described herein include using neural networks to categorize and diagnose human or other animal conditions. These systems and methods are not limited to the context of stretchable biopatches, and can be applied to other health-monitoring systems. Accordingly, when the present disclosure is described in the context of stretchable biopatches that monitor health conditions and provide wireless connectivity, it will be understood that other embodiments can take the place of those referred to.

As described above, current systems and methods for monitoring heart health of individuals includes bulky systems with bundles of cables, gelled adhesive electrode patches, tapes, and straps, which all work to inhibit everyday activities. The gelled adhesive electrodes alone significantly limit the utility of current systems. As the gels used to provide a level of conduction between the surface of the skin and the electrode dry, the ECG signal received by the electrode degrades over time. Additionally, the gels and adhesives used in the electrode patches can also cause significant skin irritation, particularly for neonatal patients.

Many of the ECG devices on the market also fail to provide information beyond ECG signals. For example, in some embodiments, it may be desirable for an ECG-monitoring device to also comprise a motion detection feature, so as to detect if the person has experienced a fall. Data from the ECG, which may indicate a category of abnormal heart rhythms, combined with data about the patent's motion activity, may help a provider determine if intervention is necessary, e.g., the abnormal heart signal may have caused the patent to fall. In some embodiments, the ECG signal and/or the motion activity may be transmitted to a system in real-time so that a provider can make immediate treatment decisions, if necessary. Current ECG-monitoring systems do not provide real-time monitoring via a monitoring network, and doctors review the ECG data retrospectively. Therefore, current devices not only fail to combine motion data along with ECG data, but they also fail to make that data available in real-time to allow timely intervention.

The present disclosure describes systems and method that can address the limitations of current health-monitoring systems. In some embodiments, the present disclosure describes a condition-monitoring device comprising a stretchable elastomer layer that can be placed upon the subject being monitored. The device may also comprise stretchable, thin-film electrodes that provide a gapless electrode-to-skin interface, obviating the need for use of conductive gels. The stretchable electrodes can be configured to stretch along with the stretchable elastomer layer. The device may also comprise a stretchable and/or flexible, thin-film circuit board that allows the electronics components of the device to bend and/or stretch with the elastomer layer. The electrodes and the circuit board may also be electronically connected via stretchable circuitry, allowing an integrated stretchable, soft construct. The circuit board may comprise a microcontroller that receives signals from the stretchable electrodes. The circuit board may also comprise additional components, such as a short-range wireless antenna and/or microelectromechanical system (MEMS) devices for monitoring patient movement.

Various devices and methods are disclosed for providing stretchable biopatches that monitor health conditions and provide wireless connectivity, and exemplary embodiments of the devices and methods will now be described with reference to the accompanying figures.

FIG. 1 is a perspective view of an exemplary monitoring device 100, according to some embodiments of the present disclosure. A monitoring device 100 may comprise an elastomer layer 102. The elastomer layer 102 may be an elastic material that allows the overall monitoring device 100 to adhere and deform naturally with the skin of a human or other animal. As will be described herein, the elastic properties of the elastomer layer 102 can be altered to provide conformal contact between the elastomer layer and a layer of skin. This conformal contact, in some embodiments, can allow the monitoring device 100 to adhere to a layer of skin without extra adhesive. This conformal contact without added adhesive can decrease the irritation caused by gelled adhesive pads.

In some embodiments, a monitoring device 100 may comprise an electrode layer 104 comprising one or more electrodes 106,108,110. For example, some embodiments may include a positive electrode 106, a negative electrode 108, and a ground electrode 110. The positive 106 and negative 108 electrodes can be used to sense physiological potentials, such as ECG signals, emanating from the patient. In some embodiments, the electrodes 106,108,110 may be disposed at least partially within the elastomer layer 102 so as to protect the electrodes. At least a portion of the electrodes 106,108,110 may extend partially from the elastomer layer 102 to a position outside of the elastomer layer 102 so that an exposed portion of the electrodes 106,108,110 can contact a layer of skin.

In some embodiments, the one or more electrodes 106, 108,110 may comprise a plurality of electrode units, as will be discussed in greater detail herein, that allow the electrodes 106,108,110 to stretch with the stretchable elastomer layer 102 and maintain contact with skin. In some embodiments, the electrodes 106,108,110 may be fabricated by patterning thin gold and polyimide (PI) films followed by elastomer layer 102 lamination to provide a gapless electrode-to-skin interface, which may obviate the need for the use of conductive gels. It is contemplated that the electrodes 106,108,110 can be thin-film membranes that are patterned photolithographically and transferred to the elastomer layer 102. In some embodiments, the electrodes 106,108,110 may be fabricated as a thin-film membrane by depositing a first PI layer, a second chromium (Cr) adhesion layer, and a third thin-film gold (Au) layer. In an exemplary fabrication method, an electrode 106,108,110 may be fabricated by (1) providing a silicon wafer, (2) spin coating the wafer with Polydimethylsiloxane (PDMS), to create a donor substrate (3) spin coating a first layer of PI, (4) depositing the Cr/Au thin-film layer, (5) patterning the layers with photoresist, (6) etching the Cr/Au thin-film layer, (7) spin coating a second layer of PI, (8) patterning the layers with photoresist, (9) etching the PI to prepare the final Cr/Au conductive patterns for the electrode 106,108,110, and (10) transferring the final electrode 106,108,110 to the elastomer layer 102. Other fabrication methods may be utilized to manufacture a thin-film electrode 106,108,110, and it is contemplated that additional conductive materials may be used for a conductive electrode 106,108,110.

In some embodiments, a monitoring device 100 may comprise a stretchable circuit board 112. The stretchable circuit board 112 may comprise one or more electronics components disposed upon the stretchable circuit board 112, as will be described in greater detail herein. In some embodiments, the stretchable circuit board 112 may be disposed at least partially within the elastomer layer 102. In some embodiments, the stretchable circuit board 112 and/or any electronics components on or connected to the stretchable circuit board 112 may be fully encapsulated within the elastomer layer. As such, the elastomer layer 102 may provide a level of water resistance and protection to the internal components of the monitoring device 100. The stretchable circuit board 112 may be positioned within the elastomer at any location within the elastomer layer 102. In some embodiments, the stretchable circuit board 112 may be positioned above the electrode layer 104 to decrease the footprint of the monitoring device 100. For example, the electrodes 106,108,110 may be positioned at one side of the elastomer layer 102 and proximate the skin, the stretchable circuit board 112 can be placed at a second side of the elastomer layer 102, i.e., above (or below) the electrode layer 104.

In some embodiments, a monitoring device 100 may comprise one or more stretchable circuits 114 to provide electrical communication between the electrodes 106,108, 110 and the stretchable circuit board 112. The stretchable circuits 114 may be designed such that the stretchable circuits 114 can stretch along with the elastomer layer 102. This too can help provide an integrated stretchable, soft construct for the monitoring device 100. The stretchable circuits 114 can be meander lines, as shown in the figure, that elongate as the elastomer layer 102 is stretched. In some embodiments, stretchable circuits 114 can be meander lines that comprise a fractal design. Additional meander lines are contemplated and the stretchable circuits 114 can be designed such that the circuitry allows the elastomer layer 102 to maintain desired elastic properties.

As described above, a monitoring device 100 may be both stretchable and flexible. The elastomer layer 102, electrodes 106,108,110, stretchable circuit board 112, stretchable circuits 114, and/or additional features described herein may also provide a level of flexibility so as to conform to areas of the body. For example, a monitoring device 100 may conform to the patient, i.e., the chest of the patient, due to the flexibility of these components. Additionally, in some embodiments, a single monitoring device 100 may be suitable for both adult users and neonatal users due at least in part to the flexibility of these components.

Figure 2:
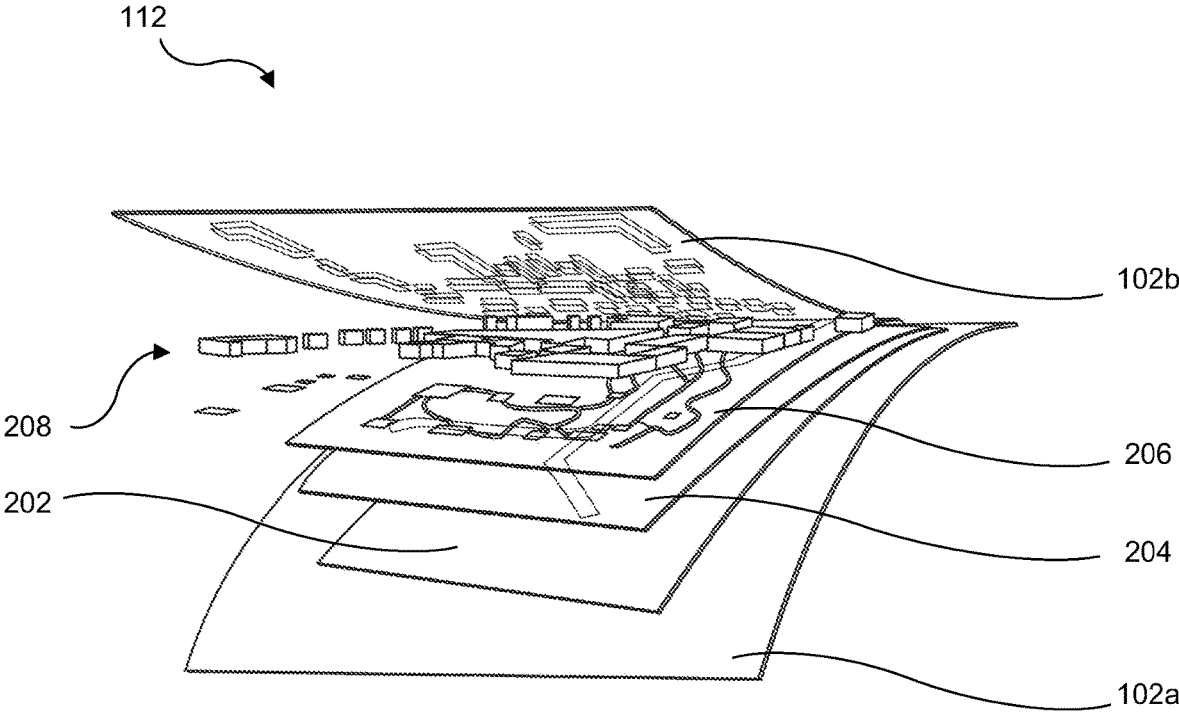
FIG. 2 is an exploded view of an exemplary stretchable circuit board, according to some embodiments of the present disclosure.

FIG. 2 is an exploded view of an exemplary stretchable circuit board 112, according to some embodiments of the present disclosure. As described herein, some embodiments of the monitoring device 100 may be designed to provide a soft, flexible, and stretchable construct to be placed upon a patient or subject. It is contemplated that the circuitry interconnection of the features of the monitoring device 100 may be made via a thin-film, on-board integrated stretchable circuit board 112. The stretchable circuit board 112 may comprise a series of thin-film electronics layers. For example, a stretchable circuit board 112 may comprise a ground plate 202. The ground plate 202 may comprise a metallic film, such as copper, and may also include a PI layer. The stretchable circuit board 112 may comprise a dielectric layer 204 to separate the ground plate 202 from an interconnect layer 206. The dielectric layer 204 may contain vias to connect the interconnect layer 206 to the ground plate 202. In some embodiments, the interconnect layer 206 may comprise a conductive material, such as copper, to electronically connect one or more electronics components connected to the stretchable circuit board 112. The one or more electronics components may be provided in a chip layer 208. In some embodiments, and as described above, each layer 202,204,206,208 of the stretchable circuit board 112 may be encapsulated in the elastomer layer 102 by a bottom elastomeric enclosure 102a and a top elastomeric enclosure 102b. Complete encapsulation, however, is not required.

In an exemplary fabrication method for creating a stretchable circuit board 112, a silicon wafer may be provided. The fabrication method may comprise spin coating the wafer with PDMS. A layer of PI may be spin coated upon the PDMS. The PI layer can be cured in an over. A layer of copper, or other conductive material, can be deposited, for example by sputtering. Next, the copper layer can be patterned with the circuit design (i.e., the interconnect layer 206) using photolithography. A second layer of PI may be spin coated upon the copper interconnects. The PI can be cured in a vacuum. The vias in the PI can be patterned using photolithography and RIE. A second layer of copper can be deposited and patterned using photolithography. A third layer of PI can be spin coated and cured in a vacuum. Finally, internal copper interconnects can be exposed by patterning the PI using photolithography and RIE. The interconnections of the one or more electronic components can then be soldered, and the stretchable circuit board 112 can be transferred to the elastomer layer 102.

13

Figure 3:
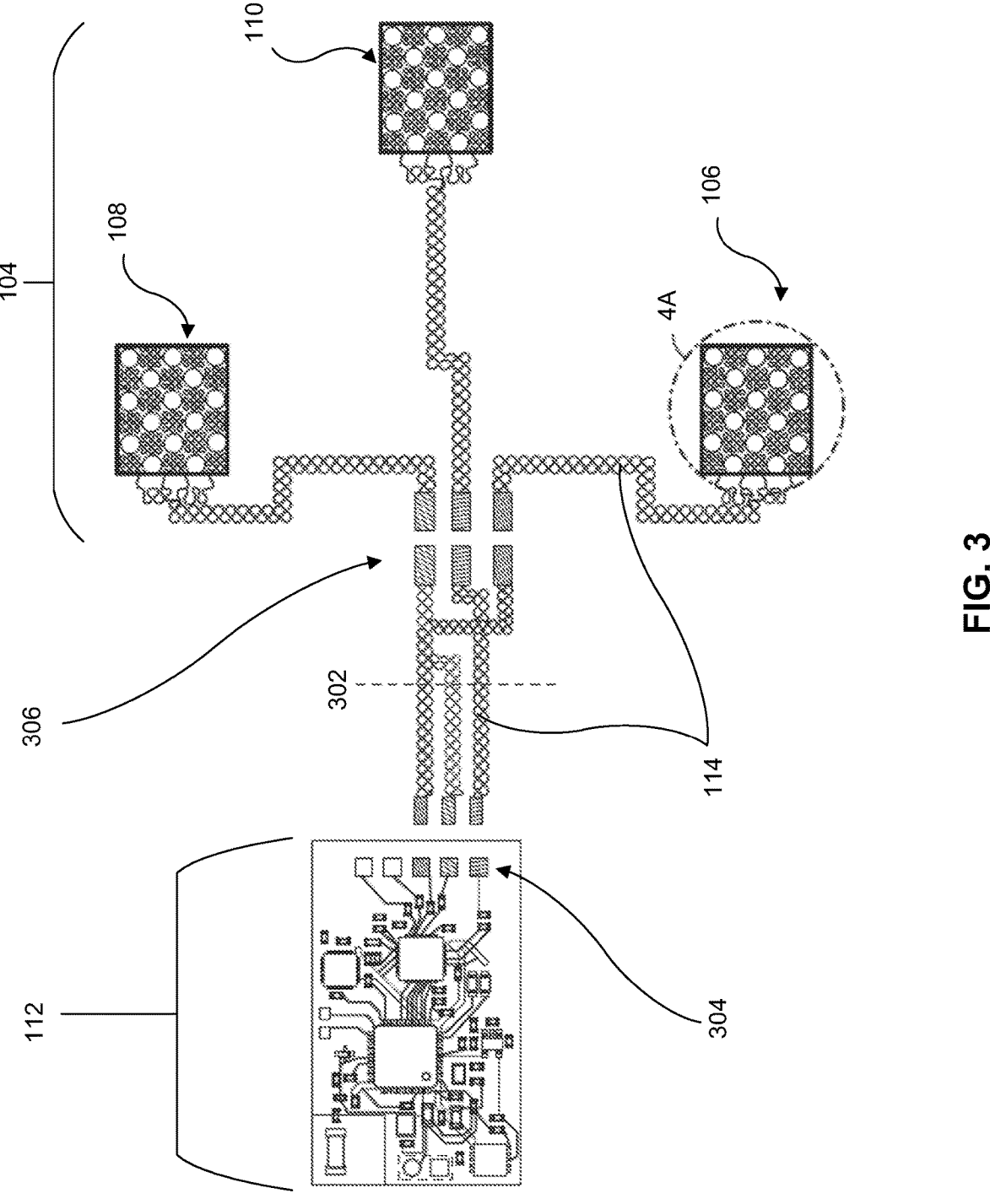
FIG. 3 is a top view of an electrode layer and stretchable circuit board, according to some embodiments of the present disclosure.

FIG. 3 is a top view of an electrode layer 104 and stretchable circuit board 112, according to some embodiments of the present disclosure. In FIG. 3, the components are not embedded in an elastomer so as to show the details of exemplary internal components of a monitoring device 100. In some embodiments, the electrode layer 104 and stretchable circuit board 112 may be placed within an elastomer layer 102 (not shown in FIG. 3) in a flat, or planar, configuration, as shown in the figure. In other embodiments, and as described above, the electrode layer 104 may be placed at a first side of the elastomer layer 102 and a stretchable circuit board 112 may be placed at a second side of the elastomer layer 102. To create this stacked construct, stretchable circuits 114 connecting the two components can be folded at a fold line 302.

In some embodiments, the electrodes 106,108,110 can be electrically connected to electrode inputs 304 of the stretchable circuit board 112 via a direct stretchable circuit 114 running to the electrode inputs 304. In some embodiments, a connection area 306 may be provided to redirect the stretchable circuits 114 to the appropriate electrode inputs 304 leads. For example, and as shown in the figure, the connection area 306 may redirect a stretchable circuit 114 coming from a negative electrode 108 to the appropriate negative lead of the electrode inputs 304. When folded across the fold line 302, the connection area 306 may be placed either proximate the electrode layer 104 or the stretchable circuit board 112.

Figures 4A, 4B, 4C:
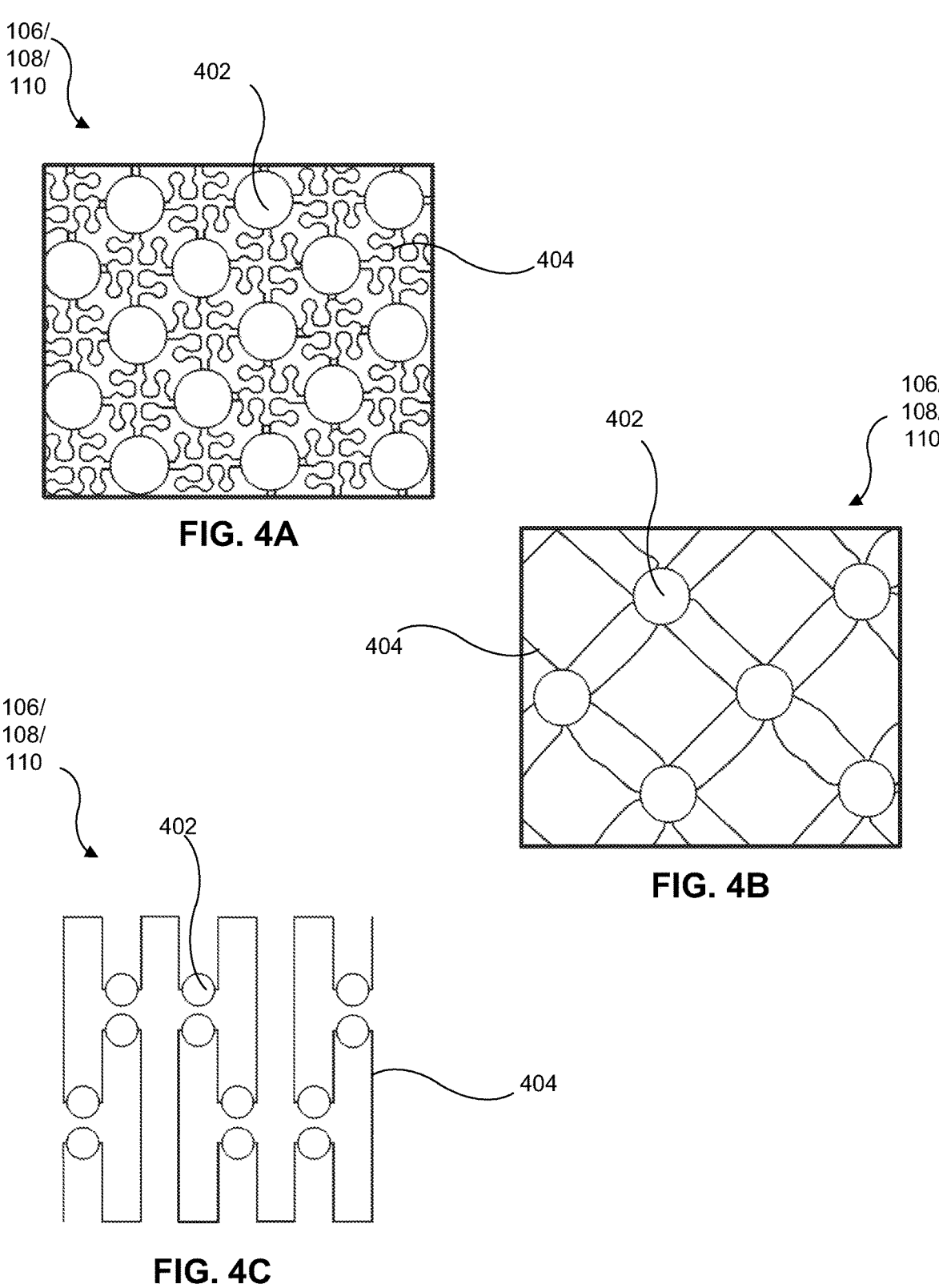
FIG. 4A is a detailed view of an exemplary electrode in a non-stretched configuration, according to some embodiments of the present disclosure.
FIG. 4B is a detailed view of an exemplary electrode in a stretched configuration, according to some embodiments of the present disclosure.
FIG. 4C is a detailed view of an exemplary electrode in a non-stretched configuration, according to some embodiments of the present disclosure.

FIG. 4A is a detailed view of an exemplary electrode 106,108,110, according to some embodiments of the present disclosure. It should be noted that FIG. 3 indicated FIG. 4A is detailed view of a positive electrode 106. However, the detailed views of the electrodes in FIGS. 4A-4C are not limited to positive electrodes 106, and the same or similar designs can be used for any other electrode, including a negative electrode 108 and/or a ground electrode 110. In some embodiments, an electrode 106,108,110 may comprise one or more electrode units 402. The one or more electrode units 402 may allow the electrodes 106,108,110 to stretch with the elastomer layer (not shown in FIG. 4A) while maintaining conformal contact with the skin. In some embodiments, each of the one or more electrode units 402 may be in electrical communication with one another by a series of stretchable electrode-unit circuits 404. For example, each electrode unit 402 of an electrode 106,108,110 may be electrically interconnected by the stretchable electrode-unit circuits 404, and each electrode 106,108,110 can be electrically connected to the stretchable circuit board 112 via stretchable circuits 114 (not shown in FIG. 4A). This may allow each electrode 106,108,110 to stretch with the elastomer layer 102 yet maintain conformal contact with the skin at each electrode unit 402.

Referring again to FIG. 4A, stretchable electrode-unit circuits 404 may be meander lines, similar to the design described for the stretchable circuits 114 in FIG. 3. The meaner lines can elongate as the elastomer layer 102 is stretched. In some embodiments, the stretchable electrode-unit circuits 404 can be meander lines that comprise a fractal design. Additional meander lines are contemplated and the stretchable electrode-unit circuits 404 can be designed such that that the circuitry allows the elastomer layer 102 to maintain desired elastic properties.

FIG. 4A shows a collapsed, unexpanded electrode 106, 108,110. FIG. 4B shows the exemplary electrode 106,108, 110 of FIG. 4A in an expanded form. As can be seen the stretchable electrode-unit circuits 404 allow the plurality of electrode units 402 to separate from each other to stretch with the elastomer layer 102 and maintain contact with skin. FIG. 4C depicts an alternative embodiment wherein the stretchable electrode-unit circuits 404 are Peano-shaped fractal designs, which is in accordance with some embodiments. Other meander lines for stretchable electrode-unit circuits 404 are contemplated and the designs are not limited by those shown in the figures.

Figure 5:
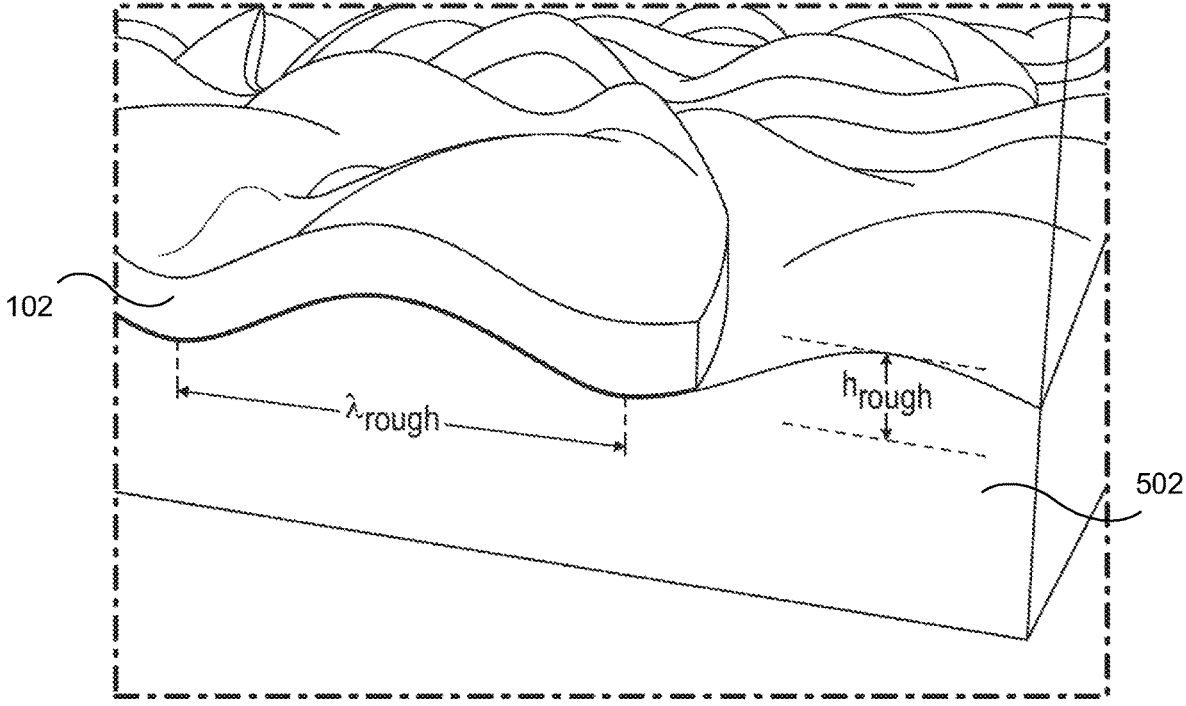
FIG. 5 depicts an elastomer layer laminating to a skin layer, according to some embodiments of the present disclosure.

FIG. 5 depicts an elastomer layer 102 laminating to a skin layer 502, according to some embodiments of the present disclosure. In some embodiments, a monitoring device 100 may adhere to a skin layer 502 via a natural adhesion of the elastomer layer 102 to the skin. In other words, in some embodiments use of an extra adhesive may not be required to adhere the monitoring device 100 to a skin layer 502. As will be appreciated, the elastomer layer 102 can have a thickness that can be modified based on desired properties of the elastomer. For example, a thick elastomer layer can provide a more durable and robust monitoring device 100. A thin elastomer layer can provide a greater degree of conformal contact with the skin layer 502.

While the increased substrate thickness ensures the electrode 106,108,110 integrity during device handling and retrieval, the added thickness may influence the level of conformal contact, which may affect ECG quality. Since conformal contact of the electrodes 106,108,110 is dependent upon design and material properties, an analytical model of the interfacial mechanics can be applied to understand the criteria for conformal contact using variables that represent skin's roughness ($\lambda_{rough}$ and $h_{rough}$, as shown in FIG. 5). Conformal contact occurs when adhesion energy is greater than the sum of the skin's elastic energy and the electrode's 106,108,110 bending energy. Adhesion energy is based on the material of the elastomer layer's 102 work of adhesion ($\gamma_{elastomer}$) and exposed surface area. The elastic energy depends on the modulus of skin ($E_{skin}$) and $\lambda_{rough}$. Bending energy can be determined by modeling the electrode based on the materials used in the electrodes 106,108, 110. For example, and as described above, an electrode may be a composite of Au, Cr, and PI. Accordingly, bending energy can be determined by modeling a composite of Au, Cr, PI, and elastomer material, contributing to an effective bending stiffness (EI).

In some embodiments, the relationship between $\gamma_{elastomer}$ and modulus ($E_{elastomer}$) can indicate how to improve conformal contact of the electrode. The following characteristics may help define the relationship. The on-board electronics of the monitoring device are assumed to be mechanically independent of the underlying electrodes and interconnects. Electrode design and layer thickness are held constant. For a given $E_{elastomer}$, there is a minimum $\gamma_{elastomer}$ that may provide conformal contact. This critical adhesion value may be expressed by:

$$\gamma_{elastomer} > \left(\frac{1}{1-\alpha}\right) \frac{\dfrac{\pi^4 EIh^2}{\lambda_{rough}^4} + \dfrac{\pi E_{skin}(h_{rough}-h)}{16\lambda_{rough}}}{\left(1 + \dfrac{\pi^2 h^2}{4\lambda_{rough}^2}\right)} \qquad \text{Equation 1}$$

In Equation 1, h can be defined as:

$$h = \frac{E_{skin}h_{rough}}{\dfrac{16\pi^3 EI}{\lambda_{rough}^3} + E_{skin}} \qquad \text{Equation 2}$$

and $\alpha$ is the areal fraction of PI and Au.

Figure 6A:
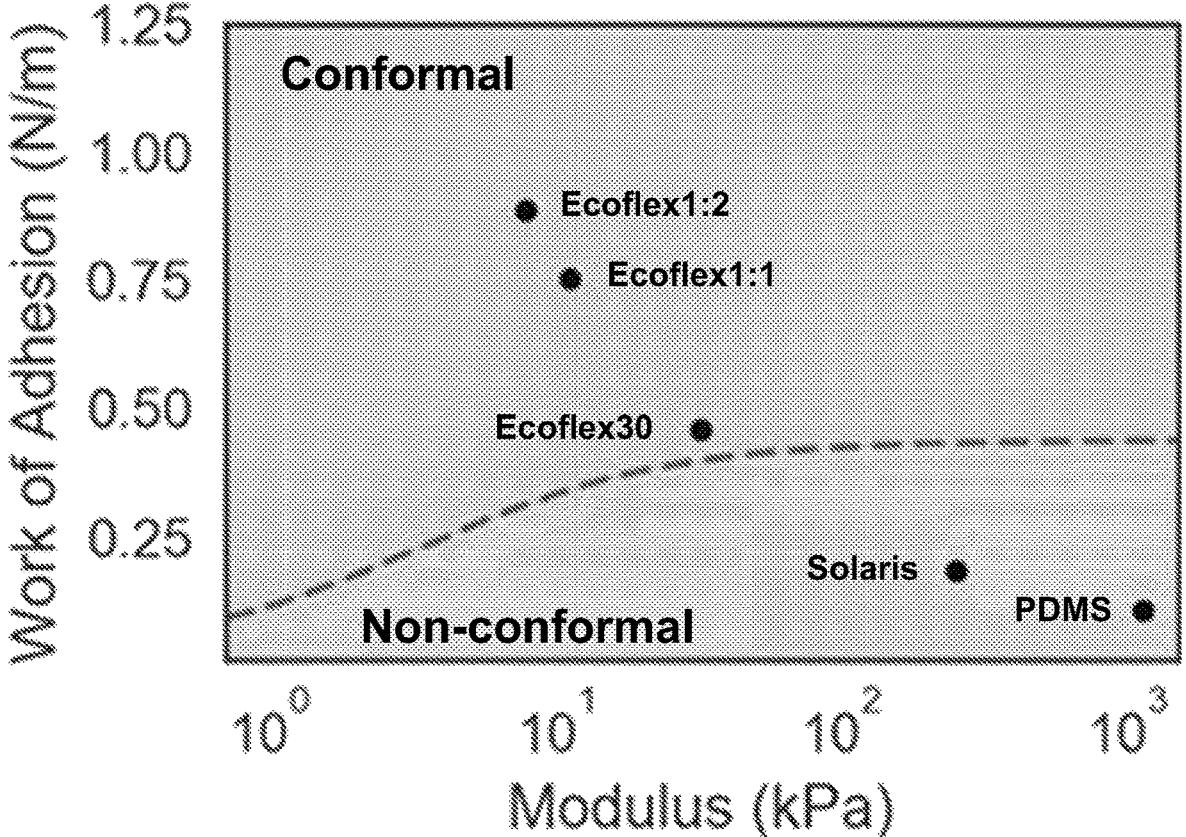
FIG. 6A is a graph depicting the conformal contact and critical points of an several elastomer materials.

FIG. 6A is a graph depicting the conformal contact and critical points of an several elastomer materials, wherein the thickness of the elastomer layer 102 was set to be 500 µm. The dotted boundary curve shown in 6A represents the critical points, and those critical points indicate the properties that may allow the 500 µm-thick elastomer to achieve conformal contact. The model calculated the work of adhesion of elastomers comprising four exemplary materials: (1) polydimethylsiloxane (PDMS) with a base-to-cure ratio of 10:1, (2) Solaris® (Smooth-On), (3) Ecoflex™ 0030 (Smooth-On), and (4) Ecoflex™ GEL (Smooth-On). The Ecoflex™ materials were modified to create usable elastomer layers. The first modification was prepared by adding an equal part of Ecoflex™ GEL to Ecoflex 0030 (referred to as 'Ecoflex1:1'), and the second modification was prepared by adding two parts of Ecoflex GEL to Ecoflex 0030 (referred to as 'Ecoflex1:2'). The measured moduli for Ecoflex1:1 and 1:2 hybrids were measured to be 11.17 kPa and 7.85 kPa, respectively. The measured moduli for PDMS and Solaris® were 1131.04 kPa and 251.53 kPa, respectively.

Experiments to obtain the work of adhesion for each sample were conducted by rolling metal cylinders down a track coated with each elastomer and observing the effective changes in the peel energy ($\Delta\gamma$) at various speeds. The rolling speeds were varied by using five cylinders with different dimensions and varying the track's angles of incline (5°, 10°, 20°, and) 30°. The set of data points for each elastomer allows the work of adhesion to be determined by finding the y-intercept of the curve fit line.

As shown in FIG. 6A, PDMS and Solaris® were categorized as non-conformal, Ecoflex 0030 as conformal with a small margin, and Ecoflex1:1 and 1:2 as conformal with a large margin. FIG. 6A also shows that conformal contact can be achieved with materials exhibiting a work of adhesion value of greater than or equal to approximately 0.50 N/m. For materials with lower moduli, the work of adhesion values can be lower. For example, a material with a low modulus may achieve conformal contact with skin with work of adhesion values greater than or equal to approximately 0.25 N/m. By using materials with lower moduli, the work-of-adhesion values required for conformal contact can be yet lower than 0.25 N/m.

Figure 6B:
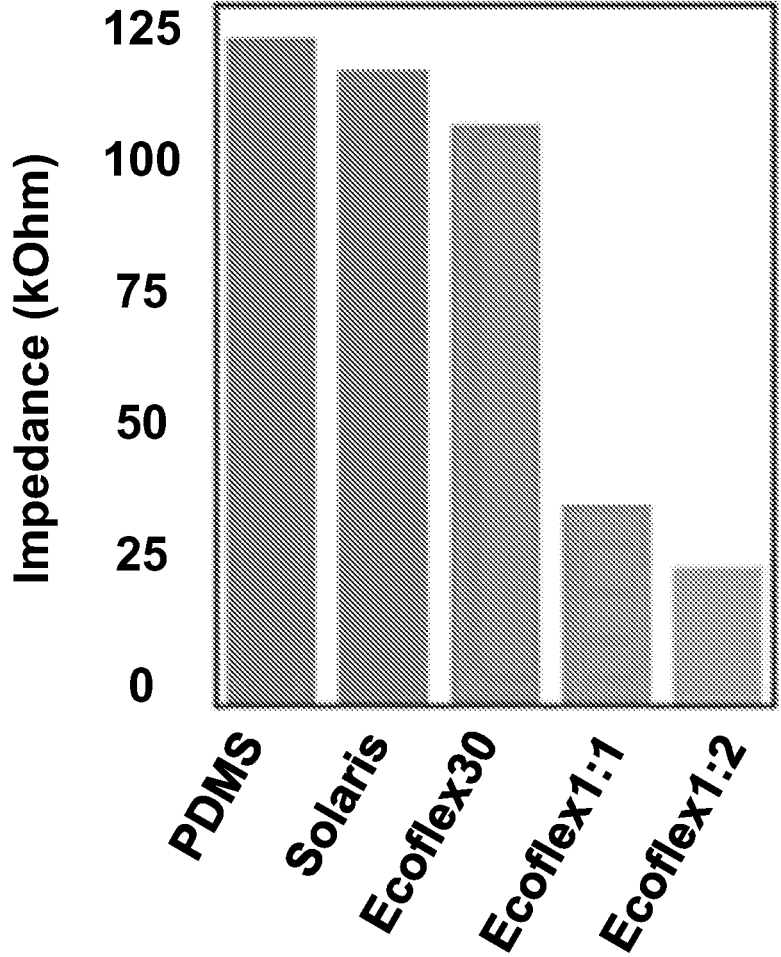
FIG. 6B is a graph showing the results of testing the electrode-to-skin contact impedance (Zc) of the elastomers described in FIG. 6A.

Non-conformality of the elastomer and electrodes may result in decreased effective electrode area and may reduce the amplitudes of the acquired ECG. Moreover, the gaps formed between the skin and metal film electrodes can deteriorate the signal qualities by introducing significant motion artifacts due to the movement-induced changes in the resistance and capacitance properties of the interface. FIG. 6B depicts the results of testing the electrode-to-skin contact impedance ($Z_c$) of the elastomers described in FIG. 6A. A low $Z_c$ may help improve acquisition of low-frequency biopotentials, such as ECG. The measurements were completed by placing the electrodes over a forearm, which had been cleansed with tape (three times) and an alcohol wipe and connecting the positive and negative electrodes to test equipment. FIG. 6B shows that the contact impedance for the five sets of electrodes followed the same order found in $E_{elastomer}$ and $\gamma_{elastomer}$, with Ecoflex 1:2 and PDMS exhibiting the lowest and highest impedances, respectively.

Figure 6C:
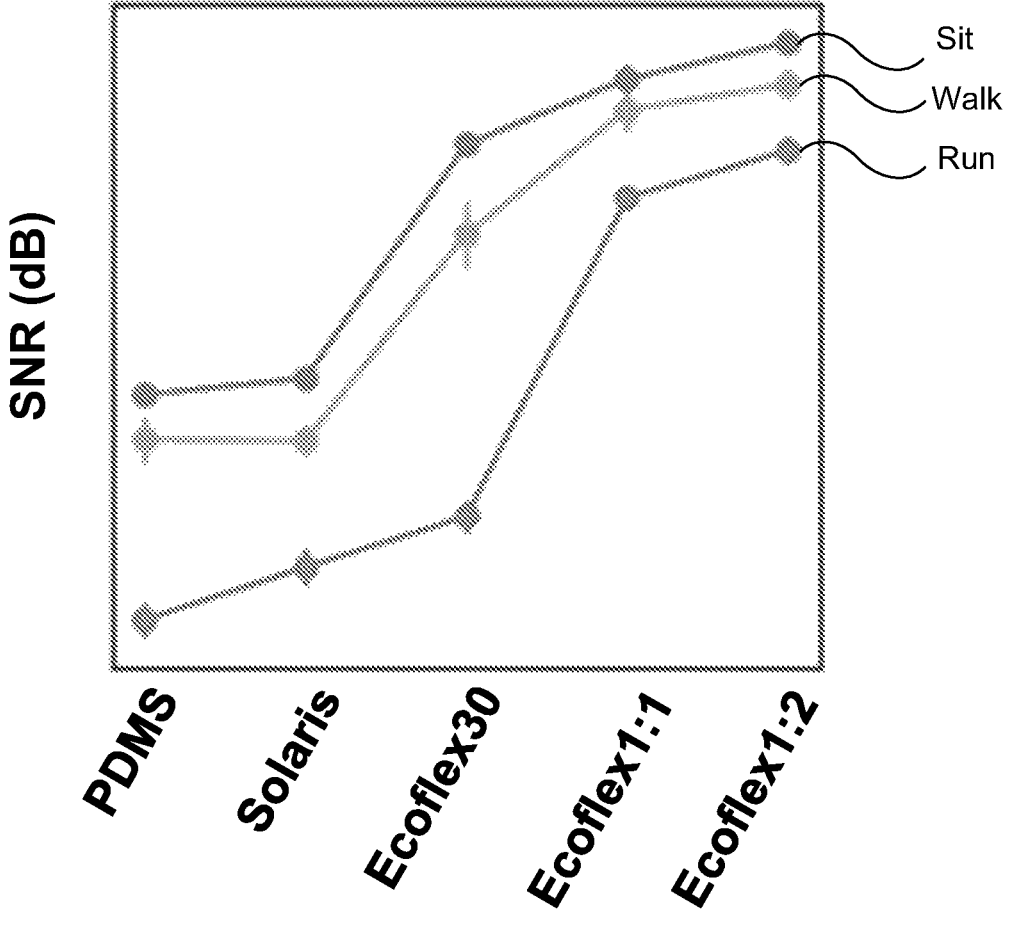
FIG. 6C is a graph of the SNR to the elastomers described in FIG. 6A.

To examine how the measured contact impedance influences acquisition of ECGs, ECG signals were collected using the five electrodes while a subject was stationary, walking, and running, and the SNRs for each device were compared. FIG. 6C is a graph of the SNRs for the five electrodes. As can be seen in FIG. 6C, the average trend in SNR measured by the five elastomer electrodes followed the same order as found in $E_{elastomer}$, $\gamma_{elastomer}$, and $Z_c$, with decreased SNR across all electrodes during walking and running. It will be understood that the exemplary materials described within the experiments are not limitations on the elastomer materials that may be used in a monitoring device 100. These results merely indicate sample ranges for the materials. For example, the experiments indicate possible ranges for work-of-adhesion properties. The experiments also indicate that the average trends for $E_{elastomer}$, $\gamma_{elastomer}$, $Z_c$, and SNR followed the same order. These findings provide information which can be used to modify the elastomer layers to improve conformal contact to skin, without use of an adhesive, and improve electrode signals.

Considering these parameters and calculations, it is contemplated that a thickness of the elastomer layer may be from approximately 200 µm to approximately 2 mm (e.g., from approximately 200 µm to approximately 500 µm, from approximately 200 µm to approximately 1 mm, from approximately 500 µm to approximately 1 mm, from approximately 700 µm to approximately 1.5 mm, from approximately 1 mm to approximately 1.5 mm, and from approximately 1.5 mm to approximately 2 mm). Also, the material for the elastomer layer can be modified as described herein to achieve desired characteristics.

Figure 7:
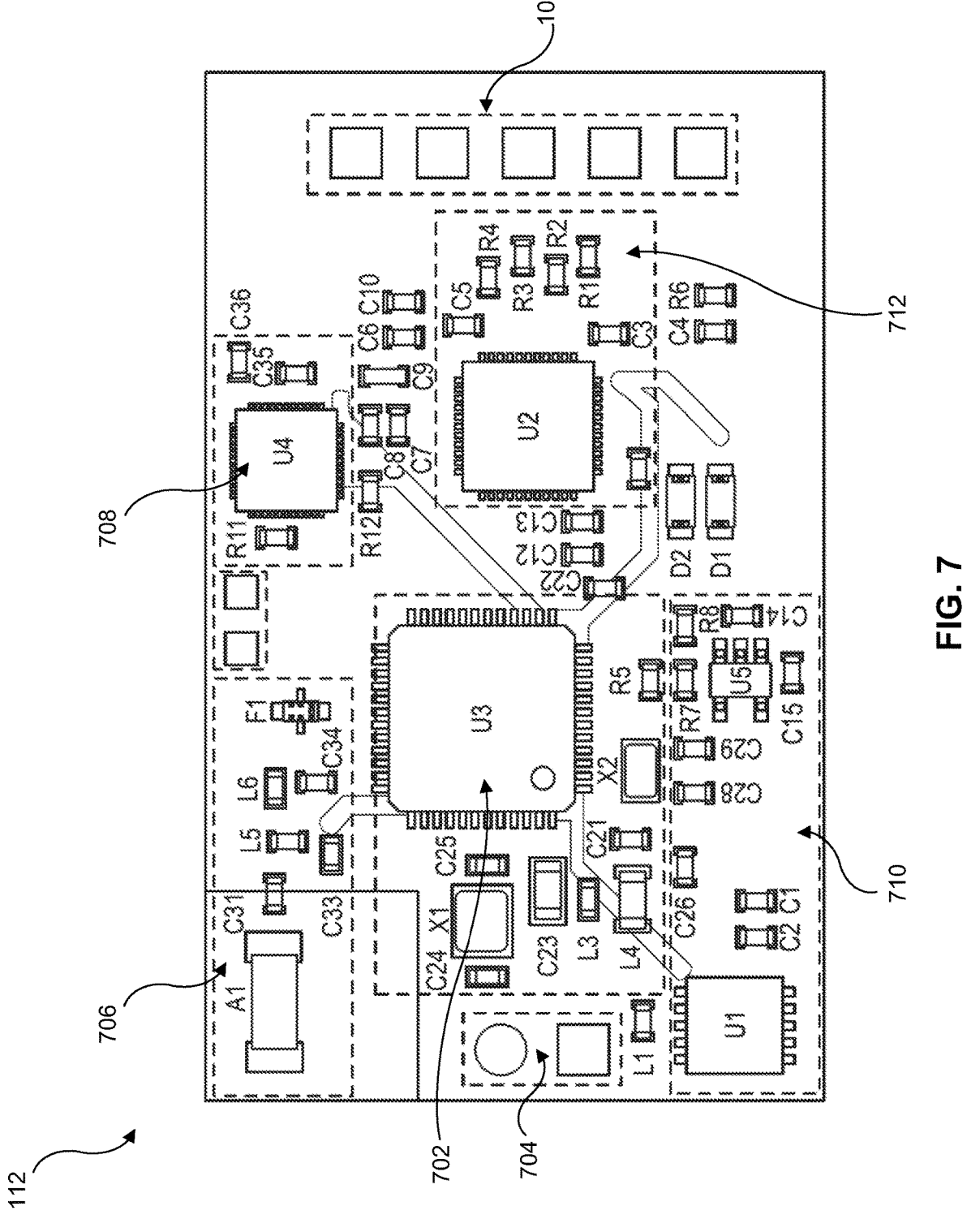
FIG. 7 is an exemplary stretchable circuit board diagram showing various exemplary electronics components, according to some embodiments of the present disclosure.

FIG. 7 is an exemplary stretchable circuit board 112 diagram showing various exemplary electronics components, according to some embodiments of the present disclosure. The component diagram is not intended in any way to limit the components capable of being disposed upon a thin-film, stretchable circuit board 112; the diagram is intended to show various exemplary electronics components which may or may not be included in a monitoring device 100.

In some embodiments, the stretchable circuit board 112 may comprise a microcontroller 702. The microcontroller 702 may comprise a processor, digital signal processor, co-processor, or the like or combinations thereof capable of executing stored instructions and operating upon data. The microcontroller 702 may perform functions related to the disclosed embodiments. For example, the microcontroller 702 may be electrically connected to the electrodes 106, 108,110 (not shown in FIG. 7) so that the microcontroller 702 can receive a voltage from the electrodes 106,108,110, wherein the voltage corresponds to the physiological potentials sensed by the electrodes 106,108,110. The electrical connection between the microcontroller 702 and the electrodes 106,108,110 may be made in part via electrical connection at electrode inputs 304. In some embodiments, the microcontroller 702 may be encapsulated within the elastomer layer 102 (not shown in FIG. 7) along with stretchable circuit board 112.

In some embodiments, the stretchable circuit board 112 may comprise a power component 704. In some embodiments, the power component 704 may comprise electrical connections that allow an external power source, for example an external battery, to connect to the stretchable circuit board 112. It is contemplated that the external power source may connect to the power component 704 via a magnetic connection. For example, as described herein, the electronics components of the monitoring device 100 may be fully encapsulated within the elastomer layer 102 of the device. In these embodiments, it is contemplated that a magnetic connecter may extend at least partially from the elastomer layer 102 so as to allow an external power source to connect to the stretchable circuit board 112. Other connectors could also allow an external power source to be connected to the stretchable circuit board 112 at a power component 704, and those additional connectors are contemplated. In other embodiments, it is contemplated that the battery may be on-board, or disposed upon the stretchable circuit board 112 at the power component 704. In these embodiments, this may allow the power source, which may be a battery, to be encapsulated within the elastomer layer 102.

In some embodiments, the stretchable circuit board 112 may comprise an antenna component 706. The antenna component 706 may be in electrical communication with the microcontroller 702 such that data processed by the microcontroller 702 can be transmitted wirelessly to an external computing device; the antenna component 706 may be in electrical communication with the microcontroller 702 such that the microcontroller 702 can receive data from the external computing device. It is contemplated that the antenna component 706 may be compatible with radio-frequency identification (RFID), near-field communication (NFC), Bluetooth™, Bluetooth™ low-energy (BLE), WiFi™, WiFi Direct™, ZigBee™, ambient backscatter communications (ABC) protocols, or similar technologies.

Figures 8A, 8B:
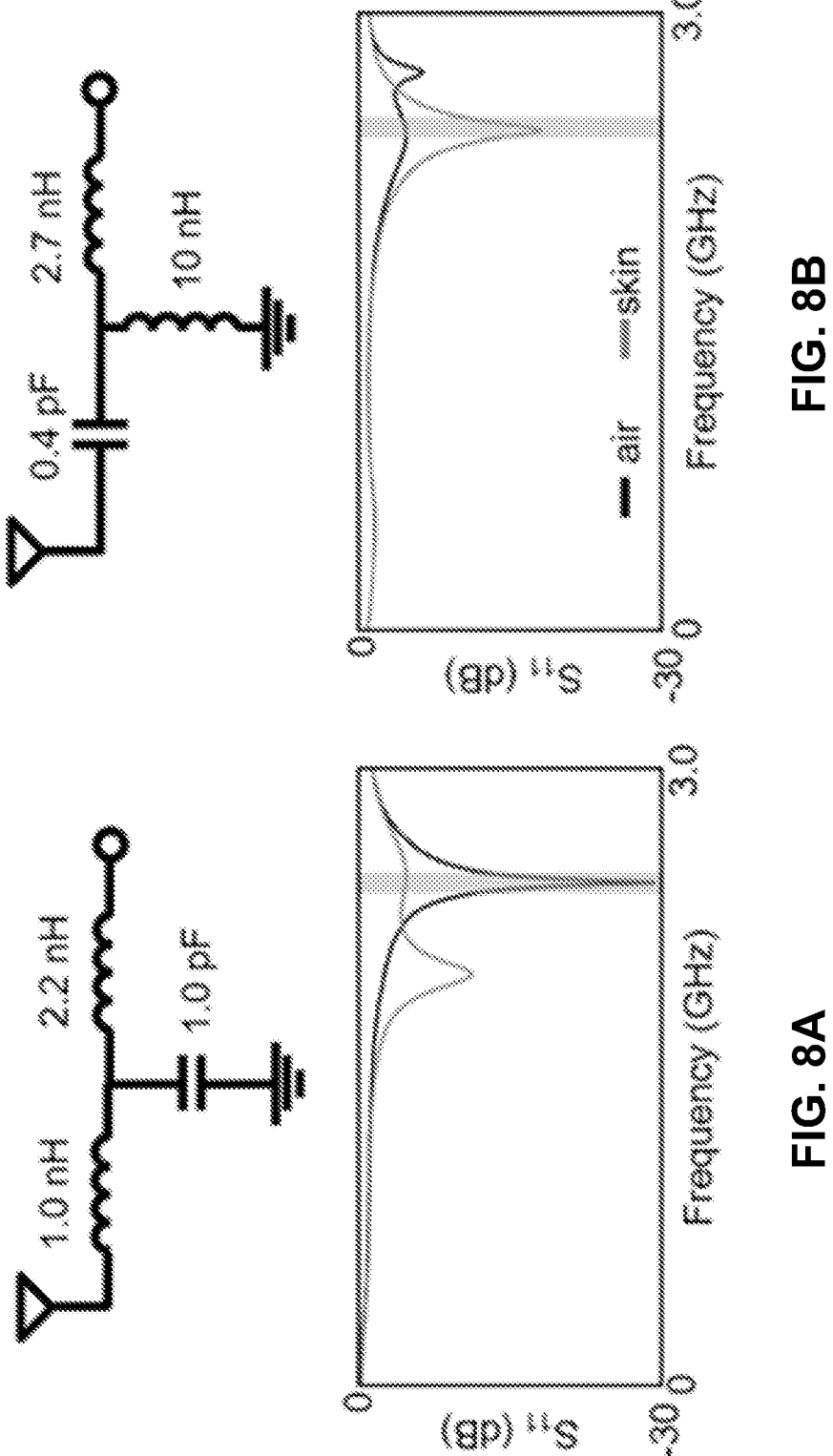
FIGS. 8A-8B depict exemplary circuits that may improve antenna signal.

A human body may affect the radiation characteristics of an antenna component 706 due to the tissue's scattering and absorption of the electromagnetic waves. Since the monitoring device 100 is designed to integrate intimately with skin, in some embodiments the long-range connectivity of the antenna may be ensured by incorporating a T-matching network with experimentally determined passive components to maximize the RF efficiency. For example and not limitation, a BLE antenna can be adjusted to maintain long-distance connectivity by providing a T-matching network with series connections of 0.4 pF capacitor and 2.7 nH inductor and a parallel connection of a 10 nH inductor, which can shift the resonant frequency of the antenna component 706 to 2.45 GHz while positioned on the chest. FIGS. 8A-8B depict an exemplary circuit that may improve the antenna component 706 signal. For example, FIG. 8A shows a BLE antenna that provides improved signal in the air, while FIG. 8B shows a BLE antenna that provides improved signal while positioned on the skin.

Referring again to FIG. 7, in some embodiments, the stretchable circuit board 112 may comprise a MEMS device 708. The MEMS device 708 may include devices that can sense motion of a patient and produce a signal. Accordingly, the MEMS device 708 may be in electrical communication with the microcontroller 702 such that the microcontroller 702 can receive and process signals produced by the MEMS device 708. It is contemplated that the MEMS device 708 may include an accelerometer, a gyroscope, and/or similar motion detecting devices. The MEMS device 708 may include a thermistor, which may be included within a single integrated unit with the accelerometer and/or gyroscope, or a thermistor can be a separate component in addition to or in combination with the accelerometer and/or gyroscope. As will be appreciated, including a motion-sensing and/or temperature sensing device may provide valuable and critical physiologic information that, in combination with the physiological potential information (e.g., ECG), can increase the effectiveness of the monitoring device 100.

In some embodiments, the stretchable circuit board 112 may comprise other electronic comments, including but not limited to voltage regulation components 710, an amplifier 712 for the signals from the electrodes 106,108,110 and/or MEMS device 708, and/or similar components. It is also contemplated that the monitoring device 100 may comprise additional sensors for tracking patient data. For example, a global positioning system (GPS) transceiver could be included in the monitoring device 100 (e.g., on the stretchable circuit board 112) to monitor patient data. For example, and not limitation, the information from the GPS could indicate whether the wearer of the device had entered the hospital. Additional sensors, such as microphones and the like, are also contemplated. All or some of the components described herein may be encapsulated within an elastomer layer 102. For example it is contemplated that all components described herein may be encapsulated in the elastomer layer 102 to provide protection, and the only exposed component of the monitoring device 100 may be at least a portion of the electrodes 106,108,110 that contact skin.

Figure 9:
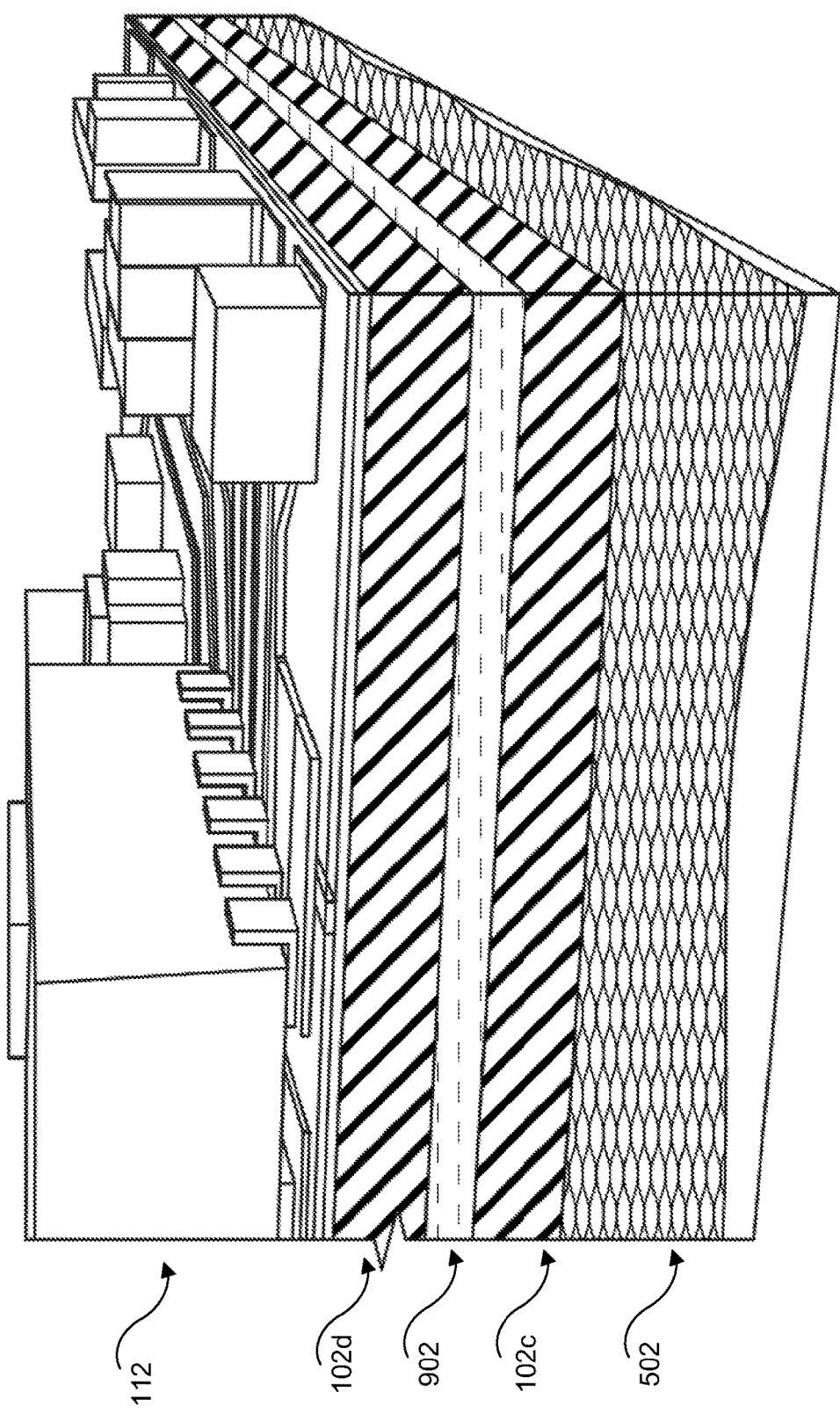
FIG. 9 is a cross section of a monitoring device showing a fluid layer disposed within the elastomer layer, according to some embodiments of the present disclosure.

FIG. 9 is a cross section of a monitoring device 100 showing a fluid layer 902 disposed within the elastomer layer 102, according to some embodiments of the present disclosure. In some embodiments, an elastomer layer 102_c,d_ may comprise a fluid layer 902 for decoupling the electrode layer 104 (not shown in FIG. 9) from the stretchable circuit board 112. As described above, the electrodes 106,108,110 (not shown in FIG. 9) may be positioned at the first side of an elastomer layer 102_d_ proximate the skin layer 502, and the stretchable circuit board 112 may be positioned at the second side of the elastomer layer 102_c_. As shown in FIG. 9, in some embodiments a fluid layer 902 may be disposed within the elastomer layer 102_c,d_ between the first side of the elastomer layer 102_c_ and the stretchable circuit board 112. The fluid layer 902 may include a fluid that may allow the electrode layer 104 to move freely with respect to the stretchable circuit board 112. The fluid may be a viscous fluid, such as vegetable oil, vegetable glycerin, mineral oil, water, and/or the like. A fluid of the fluid layer 902 may be constrained within the electrode layer 104 via elastomer encapsulation, as will be appreciated.

It is contemplated that the fluid layer 902 between the electrode layer 104 and the stretchable circuit board 112 may limit damage to the electronics not only during the normal application and removal of the device, but even from an accidental mishandling. For example, a model was developed to test the effect of the fluid layer 902 on a thin-film Cu-based stretchable circuit board 112. The model simulated an in-plane displacement (7 mm) of a circular region (diameter=3.5 mm) of the electrode layer 104 for both "with" and "without" a fluid layer 902. While 7 mm was chosen arbitrarily and is beyond the range of expected displacements during a normal use of the device, the maximum strain observed in the Cu stretchable circuit board 112 for the "with" scenario ($\varepsilon = 0.00025\%$) was a thousandth of that of the "without" scenario ($\varepsilon = 0.25\%$), which approaches the yield strain of 0.5% for a 500-nm thick Cu film. Accordingly, in some embodiments, a fluid layer 902 may be provided within the elastomer layer 102_c,d_ to prevent damage to the electronics components of the monitoring device 100.

Figure 10:
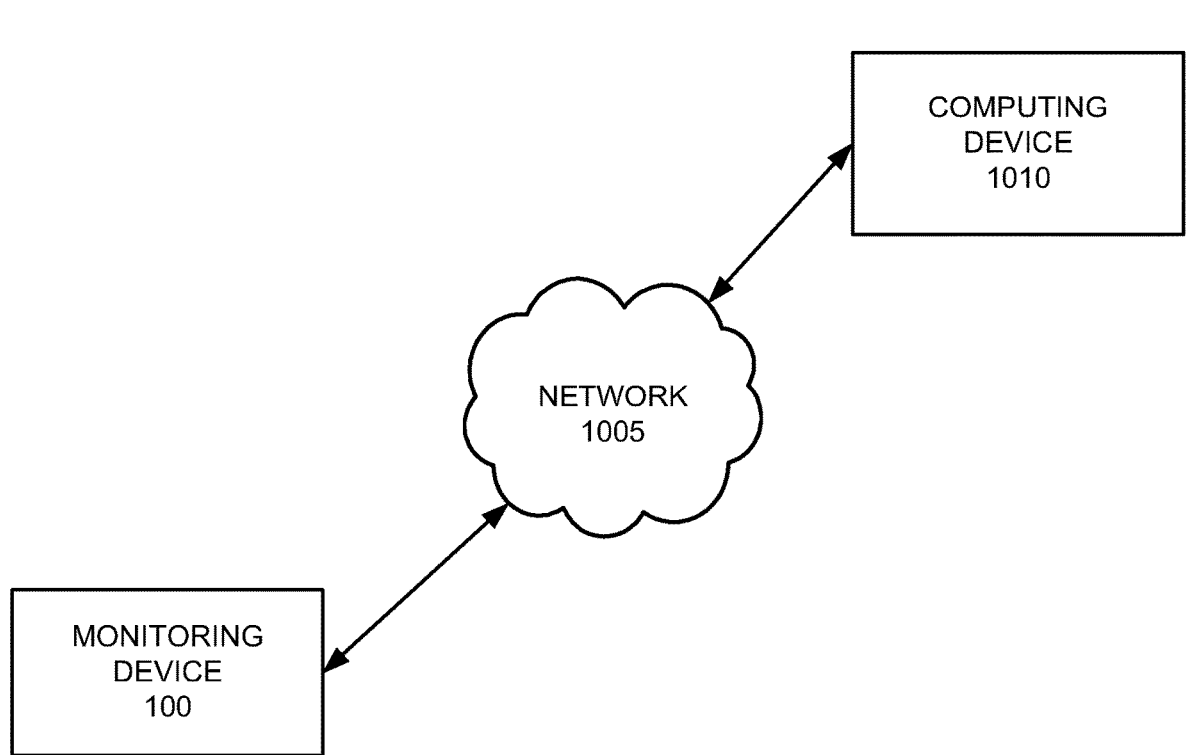
FIG. 10 is a diagram of an example system environment that may be used to implement one or more embodiments of the present disclosure.

FIG. 10 is a diagram of an example system 1000 environment that may be used to implement one or more embodiments of the present disclosure. The components and arrangements shown in FIG. 1 are not intended to limit the disclosed embodiments as the components used to implement the disclosed processes and features may vary. In some embodiments, the data obtained by the monitoring device 100 may be transmitted to a computing device 1010 for data observation, diagnostic calculations, and/or the like via a network 1005. As described herein, the network 1005 may connect the components of the system 1000 via radio-frequency identification (RFID), near-field communication (NFC), Bluetooth™, Bluetooth™ low-energy (BLE), WiFi™, WiFi Direct™, ZigBee™, ambient backscatter communications (ABC) protocols, or similar technologies. In any embodiment described herein, the computing device may include a display component allowing the wearer of the device and/or a healthcare provider to view the health data. In some embodiments, the health data can be viewed in real time.

In some embodiments, the computing device 1010 may be a mobile computing device (e.g., a smart phone, tablet computer, smart wearable device, portable laptop computer, voice command device, wearable augmented reality device, or other mobile computing device) or a stationary device (e.g., desktop computer). The computing device 1010 may be associated with the patient wearing the monitoring device 100. In some embodiments, the computing device 1010 may be associated with a health care provider. In some embodiments, the computing device 1010 may be associated with the wearer of the monitoring device 100, and the computing device 1010 may transmit the data received over the network 1005 to a health care provider via the network 1005. When the data is transmitted to a remote computing device, such as a computing device associated with a health care provider, the network 1005 may also include longer-range connections such as cellular connections. In some embodiments, the data may be transmitted to a computing device associated with a health care provider such that the health care provider can make real-time assessments of the patent and provide a timely response for emergency events, such as heart attacks and/or falls.

Figure 11:
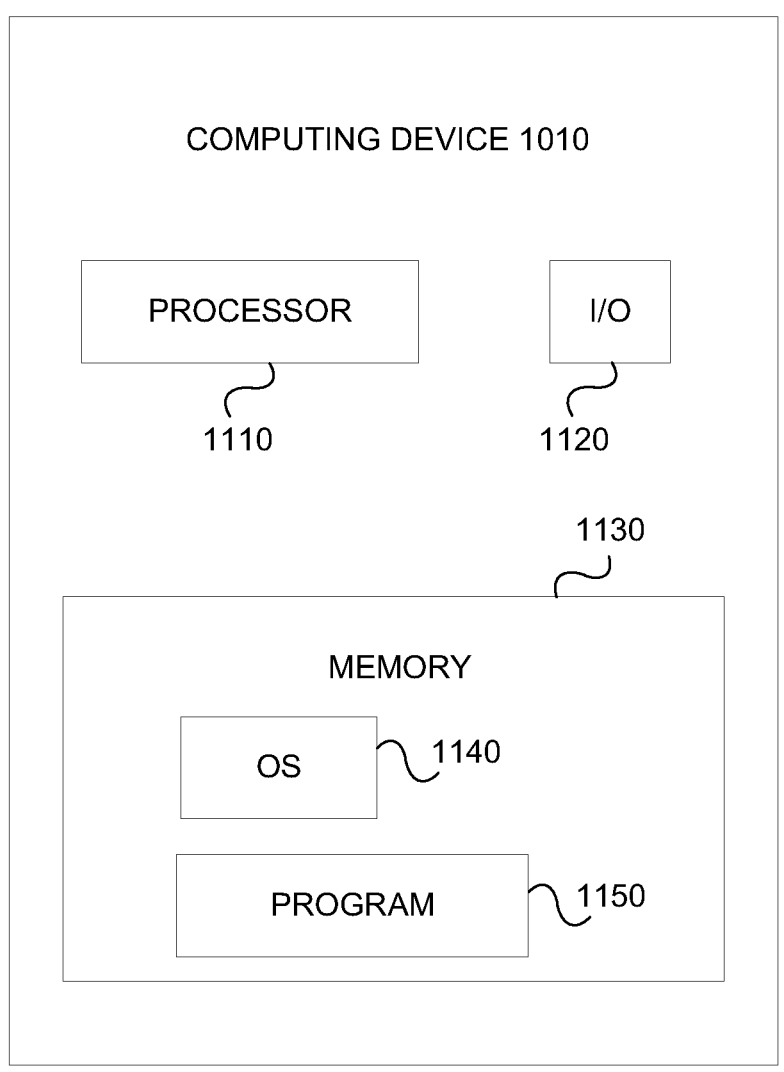
FIG. 11 depicts an exemplary component diagram for a computing device, according to some embodiments of the present disclosure.

FIG. 11 depicts an exemplary component diagram for a computing device 1010, according to some embodiments of the present disclosure. The computing device 1010 may include a processor 1110, an input/output ("I/O") device 1120, a memory 1130 containing an operating system ("OS") 1140, and a program 1150. The processor 1110 may include one or more of a microprocessor, microcontroller, digital signal processor, co-processor, or the like or combinations thereof capable of executing stored instructions and operating upon stored data. Memory 1130 may include, in some implementations, one or more suitable types of memory (e.g. such as volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like), for storing files including an operating system, application programs (including, for example, a web browser application, a widget or gadget engine, and or other applications, as necessary), executable instructions and data.

EXPERIMENTAL SECTION

Figure 12:
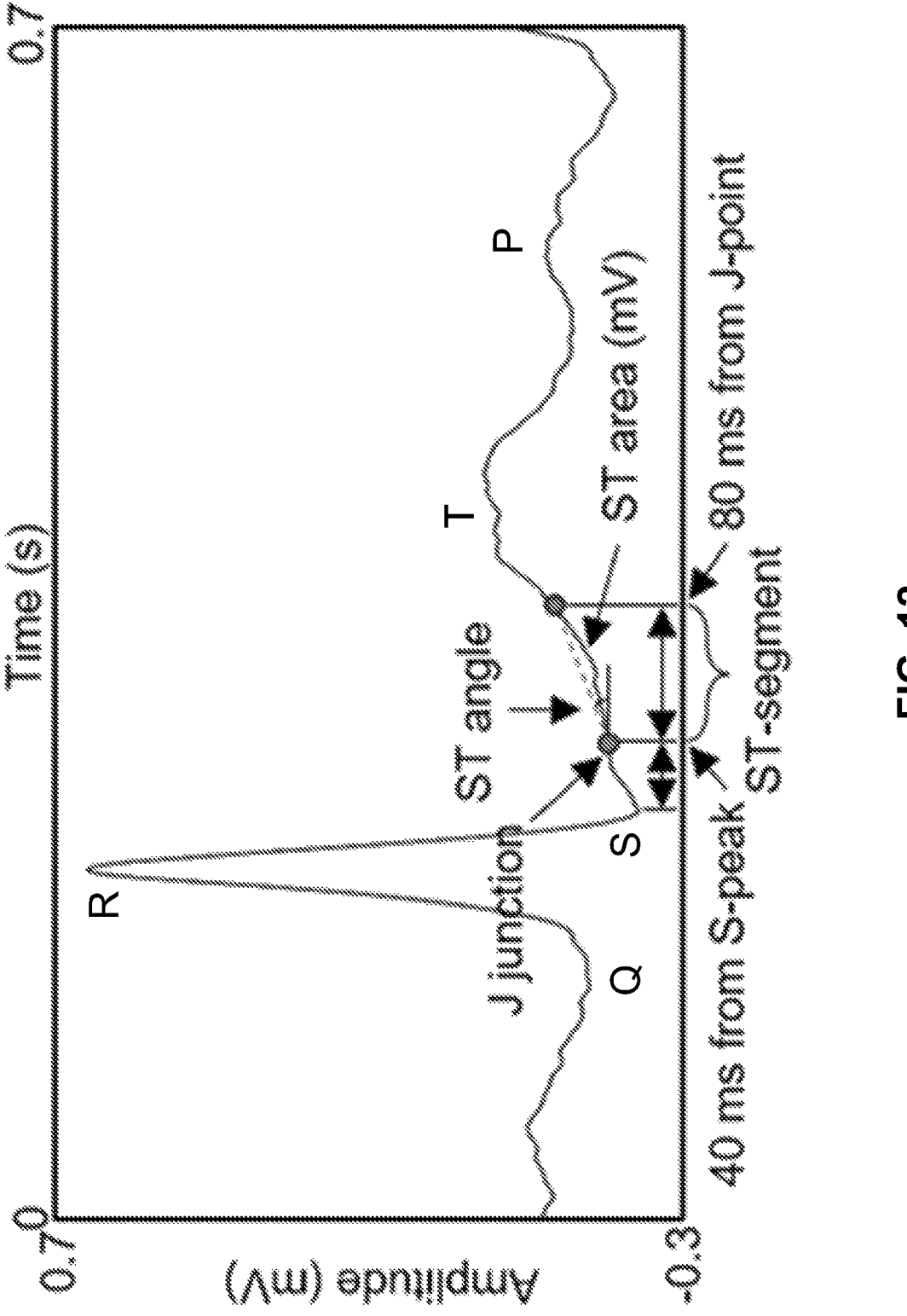
FIG. 12 depicts an ECG waveform acquired by a monitoring device, according to some embodiments of the present disclosure.

To verify the quality of ECG acquired by an exemplary monitoring device 100, waveforms were collected by exemplary devices (i.e., the device of FIG. 1 wherein the electrode layer 102 was disposed at the skin and three stretchable circuit board 112 was disposed at above the electrode layer 102). FIG. 12 depicts an ECG waveform acquired by a monitoring device 100. As shown in the figure, the monitoring device 100 is fully capable of capturing the details of the human ECG including all of PQRST complexes as well as ST-segment and J-point, the dynamics of which are useful markers associated with asymptomatic ischemia.

Figures 13A, 13B, 13C, 13D, 13E, 13F, 13G, 13H, 13I:
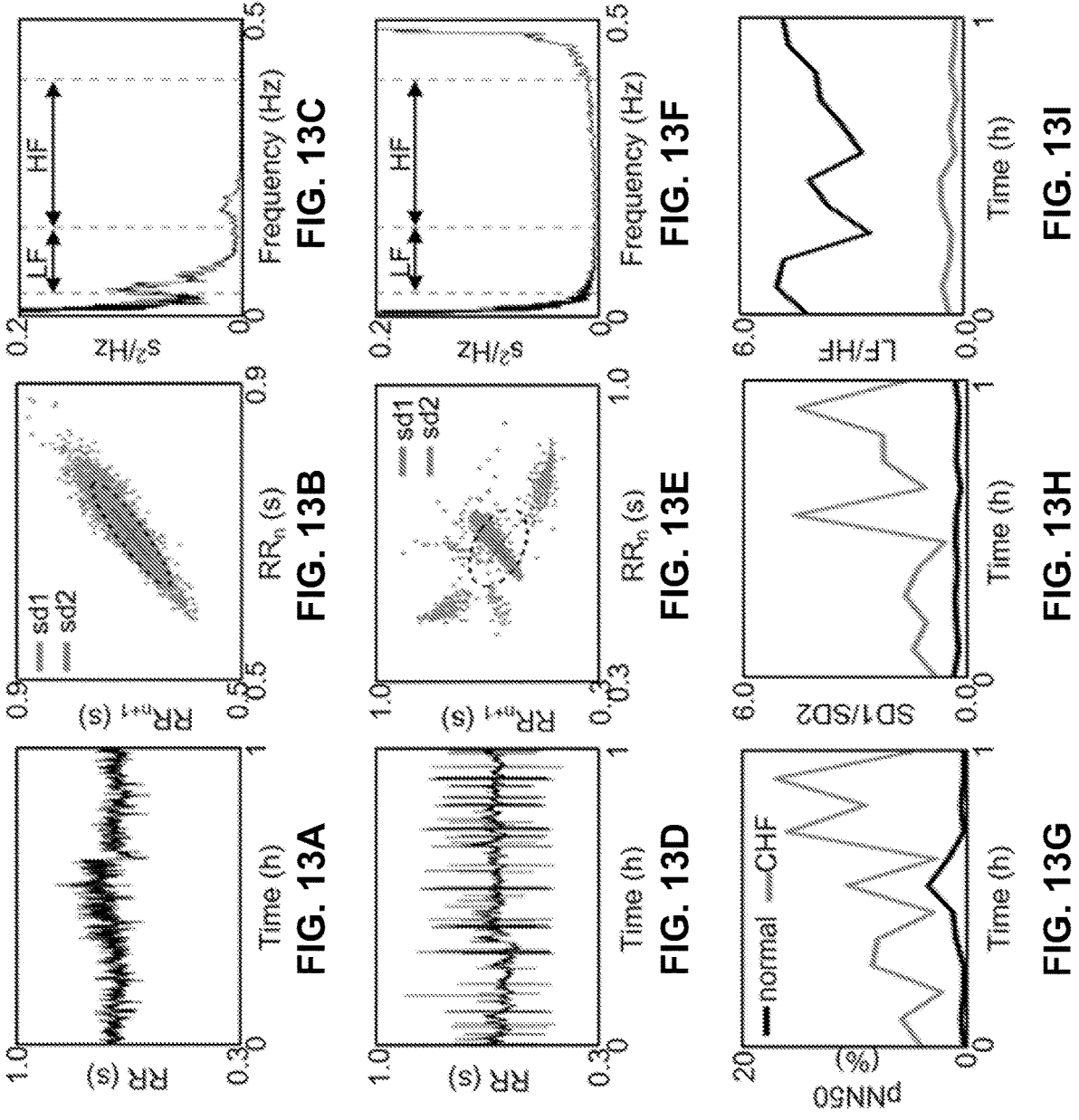
FIGS. 13A-13C show ECG waveforms acquired by a monitoring device.
FIGS. 13D-13F show ECG waveforms for heart failure patients obtained from an online database.
FIGS. 13G-13I show a comparison between critical heart failure data and the data from an exemplary monitoring device.

The acquired ECGs were also compatible with clinically relevant analysis, such as the R-R variation, low-frequency band (LF)/high-frequency band (HF) ratio, pNN50 (time domain measure of heart rate variability), and SD1/SD2 (standard deviation ratio from heart rate variability), confirming the monitoring device's 100 performance in clinically relevant ECG acquisition. FIGS. 13A-13C show ECG waveforms acquired by a monitoring device 100. In particular, FIG. 13A shows RR vs. time, FIG. 13B shows $RR_{n+1}$ VS. $RR_n$, and FIG. 13C shows a frequency spectrum. To compare the data from the monitoring device 100 to existing electrode data, FIGS. 13D-13F show ECG waveforms for heart failure patients obtained from an online database. In particular, FIG. 13D shows RR vs. time, FIG. 13E shows $RR_{n+1}$ VS. $RR_n$, and FIG. 13F shows a frequency spectrum. Comparison between the critical heart failure (CHF) data and normal data from the monitoring device is shown in FIG. 13G (pNN50), FIG. 13H (SD1/SD2), and FIG. 13I (LF/HF analyses).

Figure 14A:
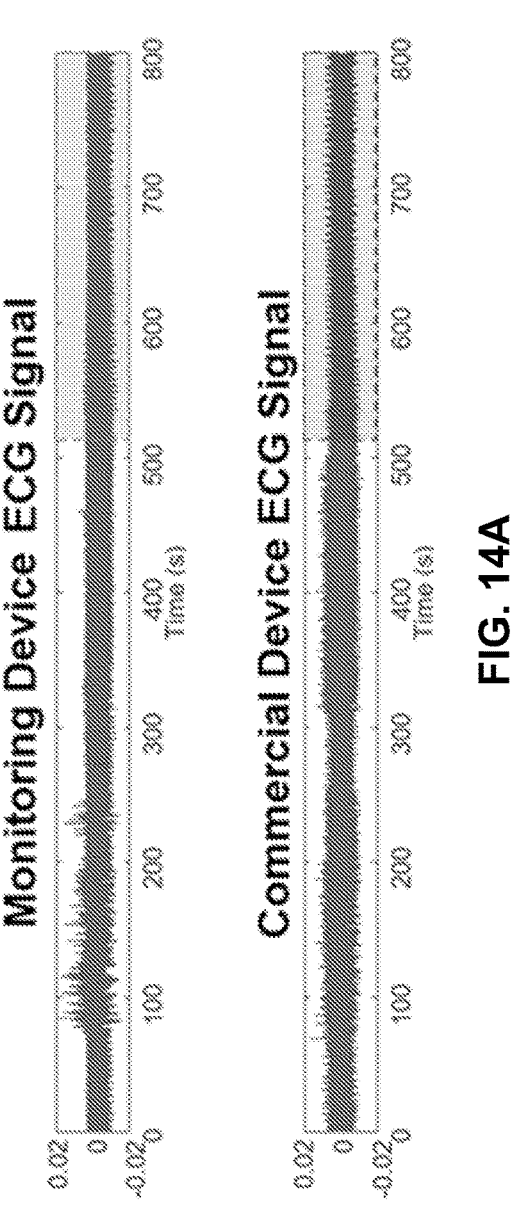
FIG. 14A is a comparison of an ECG signal produced by a monitoring device and a commercial device.
Figure 14B:
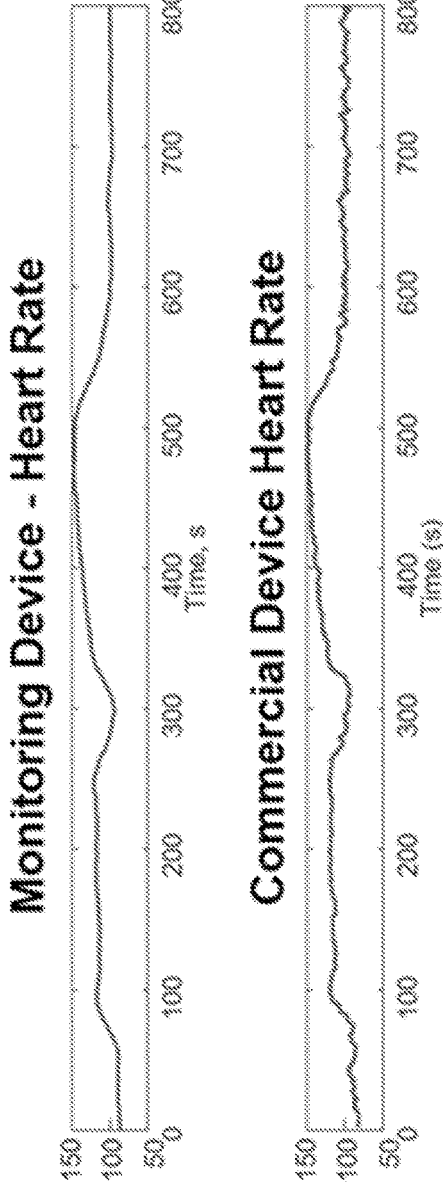
FIG. 14B is a comparison of the heart rate signal from a monitoring device and a commercial device.
Figure 14C:
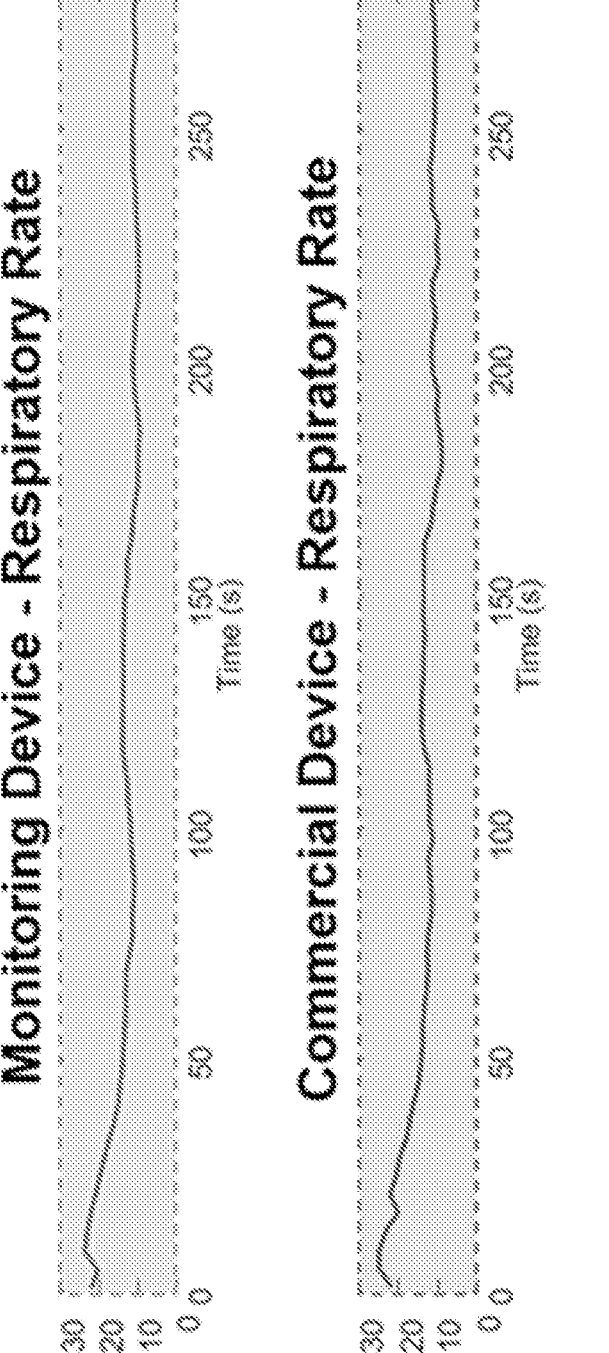
FIG. 14C is a comparison of the respiratory rate signal from a monitoring device and a commercial device.
Figures 14D, 14E:
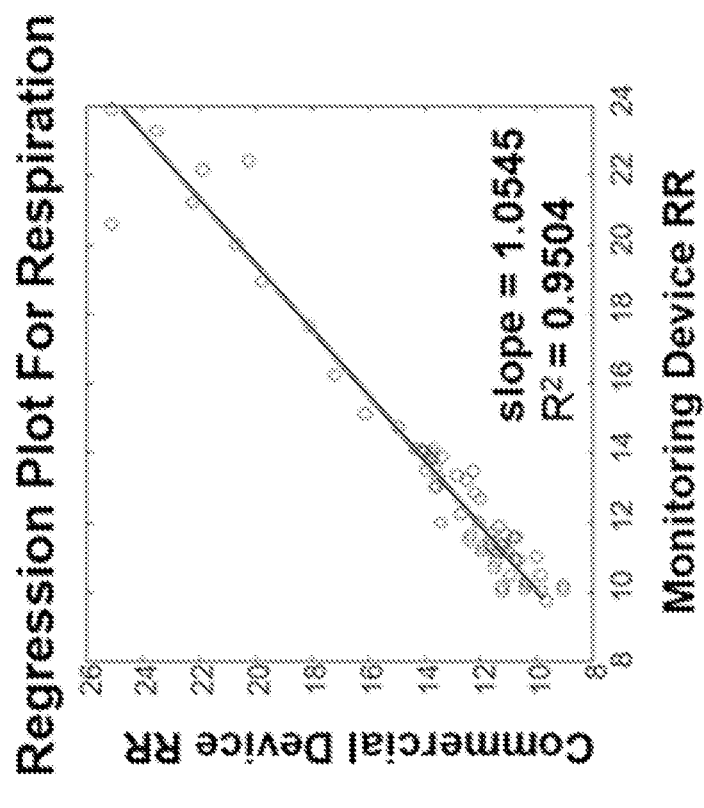
FIG. 14D is a regression plot for heart rate between a monitoring device and a commercial device, with corresponding slope and $R^2$ values.
FIG. 14E is a regression plot for respiratory rate between a monitoring device and a commercial device, with corresponding slope and $R^2$ values.

To further validate the monitoring device 100 described herein with a commercial ECG device, the heart rate and respiration rate from the monitoring device 100 was compared with those produced by a common commercial ECG device. FIG. 14A shows a comparison of the ECG signal produced by the monitoring device and the commercial device. FIG. 14B shows a comparison of the heart rate signal from the monitoring device and the commercial device. FIG. 14C shows a comparison of the respiratory rate signal from the monitoring device and the commercial device. FIG. 14D shows the regression plot for heart rate between the monitoring device and the commercial device, with corresponding slope and $R^2$ values. The regression plot shows a high coherence with a slope of 0.9760, and a coefficient of determination of R2=0.9844. FIG. 14E shows the regression plot for respiratory rate between the monitoring device and the commercial device, with corresponding slope and $R^2$ values. The regression plot also shows a good agreement with a slope of 1.0545, and a coefficient of determination of R2=0.9504. Overall, the monitoring device shows excellent performance when compared with the commercial hardware for monitoring representative physiological signals.

Common Use Examples

This present disclosure describes several systems and methods for providing flexible, stretchable biopatches that monitor health conditions and provide wireless connectivity. It is contemplated that the signals produced by the monitoring device (e.g., ECG, temperature, and/or movement) could be used to uncover deeper insights into the patient's health. Continuous wireless connectivity with increasingly powerful computing devices (e.g., computing device 1010) allows for deployment of deep learning solutions, such as machine-learning convolutional neural networks (CNNs), for real-time analysis of patient conditions. For example, and not limitation, CNNs incorporating inception-type convolutional units with residual connections may help classify user activity from acceleration and angular velocity, and may help classify semantic segmentation of ECG ectopic beats and arrhythmias for cardiac conditions. This information can be used to calculate a diagnosis based on the ECG data and/or movement data.

Figure 15:
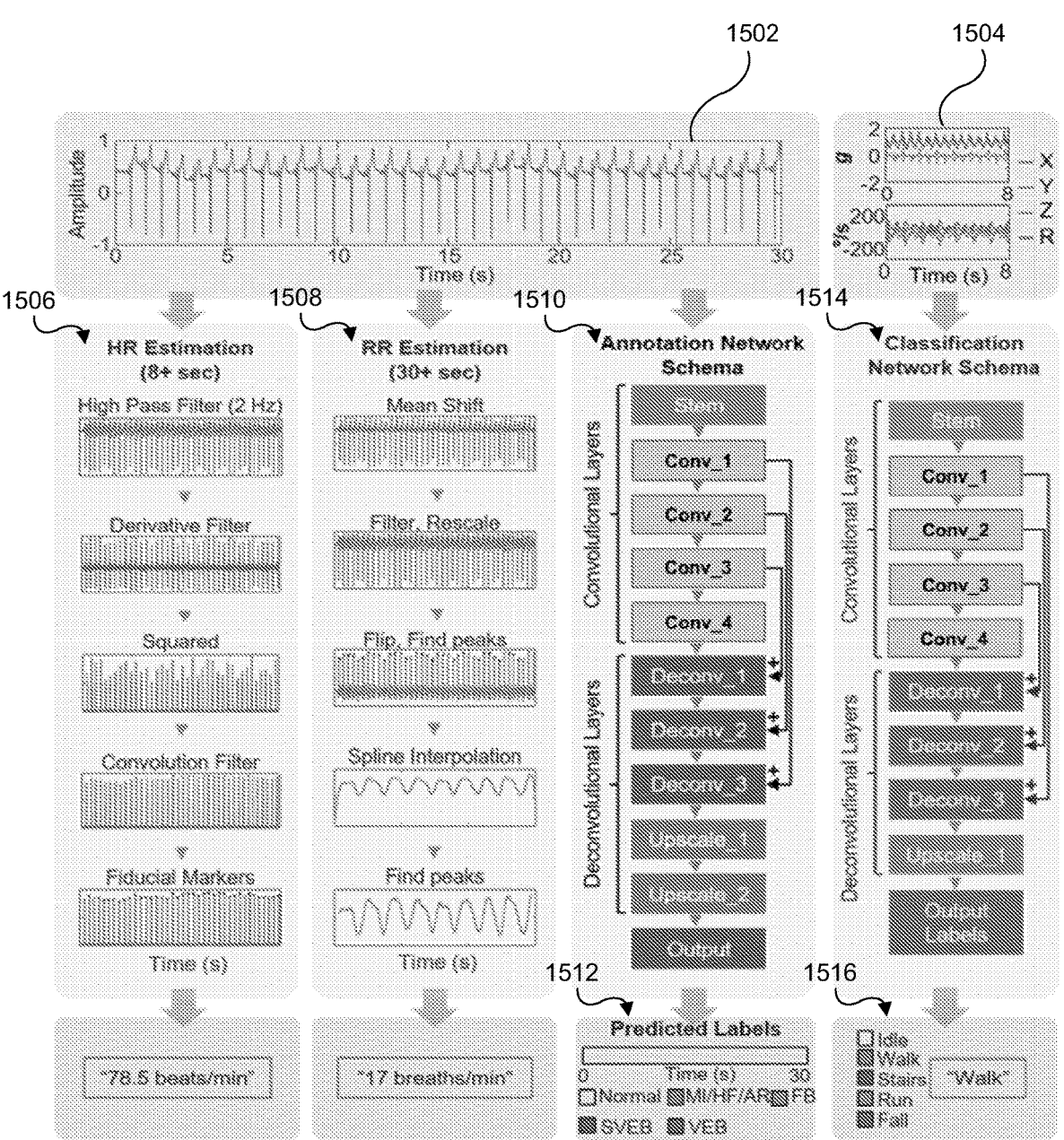
FIG. 15 is a diagram of an exemplary convolution neural network model that may output respective classifications (e.g., diagnoses) based on ECG data and movement data, according to some embodiments of the present disclosure.

In an example embodiment, the raw ECG, acceleration, and/or angular velocity data from a monitoring device 100 can be simultaneously processed toward interpreting HR, RR, ECG annotation, and activity classification. FIG. 15 is a diagram of an exemplary CNN that may output respective classifications (e.g., diagnoses) based on ECG data 1502 and movement data 1504, according to some embodiments of the present disclosure. The ECG data 1502 and the movement data 1504 can be processed either by the microcontroller on the monitoring device 100 or by computing device (e.g., computing device 1010). For the ECG data 1502, the data can be separated into HR estimation 1506 and RR estimation 1508 columns. The exemplary Annotation Network Schema 1510 column may detect various types of cardiac disease (e.g., normal sinus rhythm (normal); myocardial infarction (MI), heart failure (HF), and miscellaneous arrhythmia (AR); fusion beat (FB); supraventricular ectopic beats (SVEB); ventricular ectopic beats (VEB); and/or the like) from the ECG data 1502. The microcontroller or computing device may output predicted labels (or predicted diagnoses) 1512 for the ECG data 1502. The exemplary Classification Network Schema 1514 may process movement data 1504 to produce predicted movement diagnoses 1516. In an example embodiment, the Annotation Network Schema 1510 and/or Classification Network Schema 1514 may include a CNN, wherein, as shown in FIG. 15, the black arrows can represent residual connections (filter concatenation) between prior convolutional layers, and corresponding deconvolutional layers of similar size.

Figure 16:
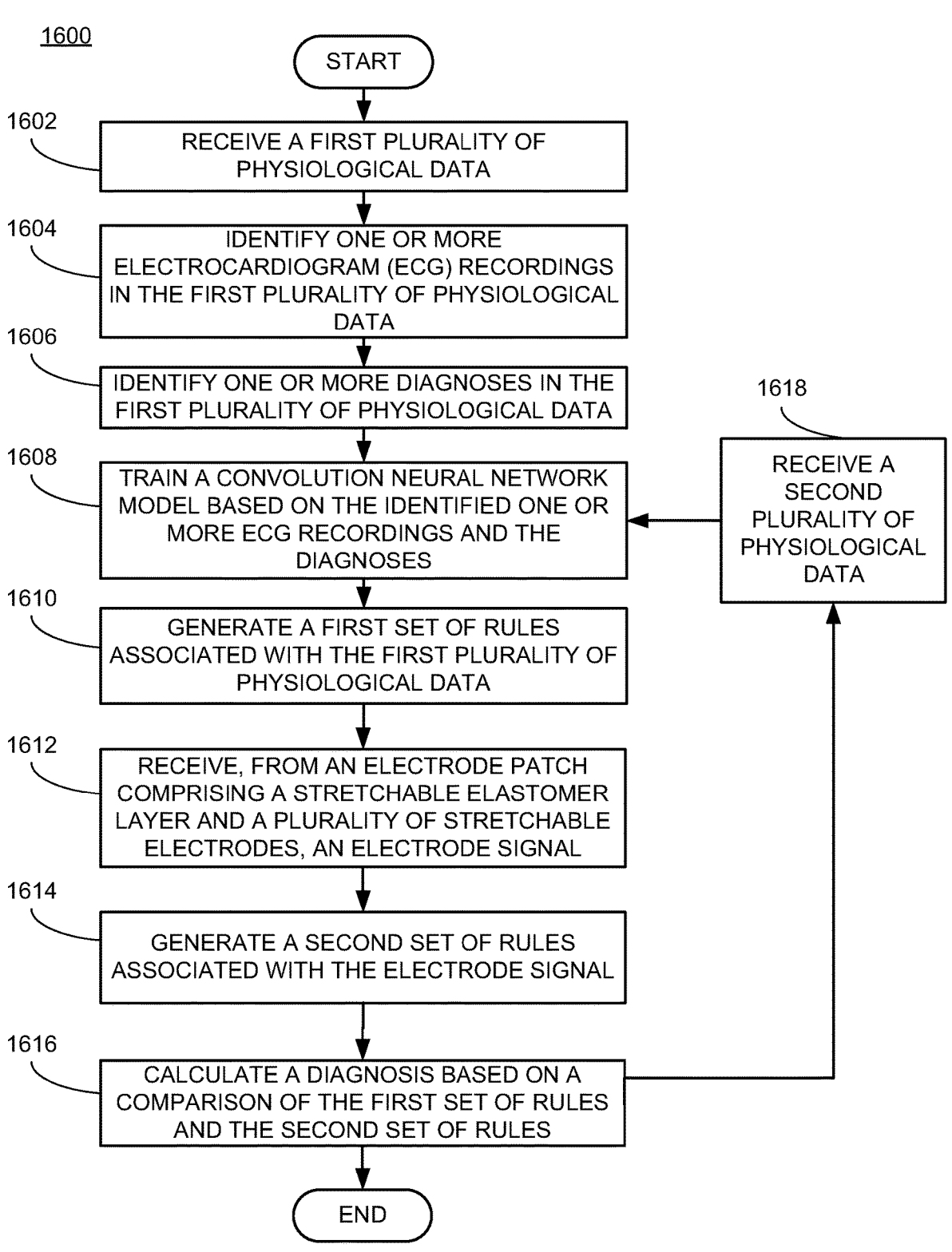
FIG. 16 is a flowchart of a method for receiving input data from a monitoring device and calculating a corresponding diagnosis, according to some embodiments of the present disclosure.

FIG. 16 is a flowchart of a method 1600 for receiving input data from a monitoring device and calculating a corresponding diagnosis. Method 1600 may be performed by a system that may include one or more of the computing devices 1010 described herein.

In block 1602, the system may receive a first plurality of physiological data. The first plurality of physiological data may be associated with a diagnostic database. For example, certain databases provide ECG data and/or movement data, and the data may also include diagnosis information that is associated with the data. In other embodiments, the first plurality of physiological data may be associated with a clinical trial. For example, the provider using the system may have a large sample of ECG data and/or movement data in which to provide to the system. The provider may also label the data individually so as to create a personalized set of comparison data.

In block 1604, the system may identify one or more electrocardiogram (ECG) recordings in the first plurality of physiological data. As described above, the first plurality of physiological data may include ECG data and/or movement data. At block 1602, this data may be identified from the first plurality of physiological data.

In block 1606, the system may identify one or more diagnoses in the first plurality of physiological data. This diagnosis information can either be present in the first plurality of physiological data or may be labeled by a health care provider manually.

In block 1608, the system may train a CNN model based on the identified one or more ECG recordings and the diagnoses. This step may also include training the CNN model based on the movement data. As described above, in some embodiments, the CNN may incorporate inception-type convolutional units with residual connections to classify (or diagnose) user activity from acceleration and angular velocity, and may diagnose semantic segmentation of ECG ectopic beats and arrhythmias for cardiac conditions.

In block 1610, the system, via the machine-learning CNN on the computing device, may generate a first set of rules associated with the first plurality of physiological data. These first set of rules may for the basis for diagnosing the ECG data as normal, MI/HF/AR, FB, SVEB, VEB, and/or the like. Additionally, if the CNN is trained on movement data, the first set of rules may be the basis for classifying the data as either idle, walking, ascending stairs, running, falling, and/or the like.

In block 1612, the system may receive, from a monitoring device 100 as described herein, an electrode signal. The system can receive the electrode signal from the monitoring device to compare with the first set of ECG signals. As described above, this step may also include receiving movement data from the monitoring device 100.

In block 1614, the system, via the machine-learning CNN on the computing device, may generate a second set of rules associated with the electrode signal and/or movement signal from the monitoring device 100.

In block 1616, the system, via the machine-learning CNN on the computing device, may calculate a diagnosis based on a comparison of the first set of rules and the second set of rules. At this step, the system is able to prepare the diagnoses based on the rules from the first plurality of physiological data and the signals transmitted from the monitoring device 100.

The method 1600 may end after block 1616. In some embodiments, the system may be re-trained based on a second plurality of physiological data. In this embodiments, the CNN may continue to learn based on additional physiological data (e.g., ECG and/or movement data). In Block 1618, the system may receive a second plurality of physiological data and begin the method 1600 again at Block 1608 to re-train the CNN. The second plurality of physiological data can be similar to the first plurality of physiological data.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A condition-monitoring device comprising:
an elastomer layer comprising a first side configured for conformal contact with a layer of skin and a second side, wherein the elastomer layer has a work of adhesion value from about 0.25 N/m to about 0.90 N/m;
a first electrode positioned proximate the first side of the elastomer layer, the first electrode comprising one or more electrode units wherein the one or more electrode units comprises at least one of a positive electrode, negative electrode, or ground electrode, and wherein one or more electrode-unit circuits electrically interconnect the one or more electrode units allowing the one or more electrode units to stretch with the elastomer layer;
a stretchable circuit board positioned proximate the second side of the elastomer layer and in electrical communication with the first electrode; and a microcontroller in electrical communication with the stretchable circuit board and the first electrode;
a fluid layer constrained within the elastomer layer and disposed between the first electrode and the stretchable circuit board, the fluid layer configured to decouple the first electrode from the stretchable circuit board.

2. The condition-monitoring device of claim 1 wherein the stretchable circuit board and the microcontroller are encapsulated within the elastomer layer.

3. The condition-monitoring device of claim 1, wherein:
a portion of the first electrode is disposed within the elastomer layer and another portion of the first electrode extends from the elastomer layer to a position outside of the elastomer layer;
the first electrode is configured to sense physiological potentials from a wearer of the condition-monitoring device and produce a voltage; and
at least a portion of the stretchable circuit board is disposed within the elastomer layer.

4. The condition-monitoring device of claim 1 further comprising:
a first stretchable circuit configured to:
provide electrical communication between the first electrode and the stretchable circuit board; and
stretch with the elastomer layer;
a second electrode positioned proximate the first side of the elastomer layer and extending at least partially from the elastomer layer to a position outside of the elastomer layer; and
a second stretchable circuit configured to:
connect the second electrode to the stretchable circuit board; and
stretch with the elastomer layer;
wherein the microcontroller is configured to receive a voltage from the first electrode via the first stretchable circuit.

5. The condition-monitoring device of claim 1, wherein properties of the elastomer layer including at least a work of adhesion value and an elastic modulus provide, at least in part, for the conformal contact.

6. The condition-monitoring device of claim 1 further comprising a microelectromechanical system (MEMS) device in electrical communication with the microcontroller.

7. A condition-monitoring device comprising:
an elastomer layer comprising a first side configured for conformal contact with a layer of skin and a second side, wherein the elastomer layer has a work of adhesion value from about 0.25 N/m to about 0.90 N/m;

a first electrode positioned proximate the first side of the elastomer layer, the first electrode comprising one or more electrode units wherein the one or more electrode units comprises at least one of a positive electrode, negative electrode, or ground electrode, and wherein one or more electrode-unit circuits electrically interconnect the one or more electrode units allowing the one or more electrode units to stretch with the elastomer layer;
a stretchable circuit board positioned proximate the second side of the elastomer layer and in electrical communication with the first electrode;
a fluid layer constrained within the elastomer layer and disposed between the first electrode and the stretchable circuit board, the fluid layer for decoupling configured to decouple the first electrode from the stretchable circuit board and allowing the first electrode to move more freely with respect to the stretchable circuit board;
a microcontroller in electrical communication with the stretchable circuit board and the first electrode; and
a microelectromechanical system (MEMS) device in electrical communication with the microcontroller;
wherein the first side of the elastomer layer is configured for the conformal contact, to adhere to the layer of skin without an adhesive when an adhesion energy of the elastomer layer is greater than a sum of an elastic energy of the skin and a bending energy of the first electrode; and
wherein:
the MEMS device is disposed on the stretchable circuit board; and
the stretchable circuit board, the microcontroller, and the MEMS device are encapsulated within the elastomer layer.

8. The condition-monitoring device of claim 7 further comprising an antenna configured to transmit a wireless signal from the microcontroller to a computing device.

9. A condition-monitoring device comprising:
an elastomer layer having a first side configured for adhesive-free, conformal contact with a layer of skin and a second side, wherein the elastomer layer has a work of adhesion value from about 0.25 N/m to about 0.90 N/m;
a positive electrode assembly comprising a first set of electrode units, wherein at least one of the electrode units of the first set is a positive electrode positioned proximate the first side of the elastomer layer, wherein one or more electrode-unit circuits electrically interconnect the first set of electrode units allowing the first set of electrode units to stretch with the elastomer layer;
a first set of stretchable circuits in electrical communication with the first set of electrode units;
a negative electrode assembly comprising a second set of electrode units, wherein at least one of the electrode units of the second set is a negative electrode positioned proximate the first side of the elastomer layer, wherein one or more electrode-unit circuits electrically interconnect the second set of electrode units allowing the second set of electrode units to stretch with the elastomer layer;
a second set of stretchable circuits in electrical communication with the second set of electrode units;
a stretchable circuit board disposed at least partially within the elastomer layer and is positioned proximate the second side of the elastomer layer, and the stretchable circuit board is in electrical communication with the positive and negative electrodes;

a fluid layer constrained within the elastomer layer and disposed between (i) the positive electrode assembly and the negative electrode assembly and (ii) the stretchable circuit board and configured for decoupling (a) the positive electrode assembly and the negative electrode assembly from (b) the stretchable circuit board;

a microcontroller electrically connected to the stretchable circuit board and in electrical communication with the positive and negative electrodes;

a third stretchable circuit configured to provide electrical communication between the positive electrode and the stretchable circuit board; and a fourth stretchable circuit configured to provide electrical communication between the negative electrode and the stretchable circuit board;

wherein the first set of stretchable circuits, the second set of stretchable circuits, the third stretchable circuit, and the fourth stretchable circuit are configured to stretch with the elastomer layer.

10. The condition-monitoring device of claim 9, wherein the stretchable circuit board is positioned proximate the second side of the elastomer layer; and wherein the stretchable circuit board and the microcontroller are encapsulated within the elastomer layer.

11. The condition-monitoring device of claim 9, wherein the first side of the elastomer layer is configured for the adhesive-free, conformal contact with the layer of skin based at least in part on one or more properties of the elastomer layer.

12. The condition-monitoring device of claim 11, wherein another one of the one or more properties of the elastomer layer is an elastic modulus.

13. The condition-monitoring device of claim 9, wherein a thickness of the elastomer layer is from 200 μm to 2 mm.

14. The condition-monitoring device of claim 9 further comprising a microelectromechanical system (MEMS) device in electrical communication with the microcontroller;

wherein the MEMS device comprises at least one of an accelerometer, a gyroscope, or a thermistor.

15. The condition-monitoring device of claim 14, wherein:

the MEMS device is disposed on the stretchable circuit board; and the stretchable circuit board, the microcontroller, and the MEMS device are encapsulated within the elastomer layer.

16. The condition-monitoring device of claim 9 further comprising an antenna configured to transmit a wireless signal from the microcontroller to a computing device;

wherein the wireless signal comprises data associated with physiological potentials.

17. A method for monitoring health conditions of a wearer of the condition-monitoring device of claim 1 comprising:

placing the condition-monitoring device of claim 1 on a wearer, wherein the first side of the elastomer layer is in conformal contact with the skin of the wearer; and receiving, at a computing device, an output signal from the microcontroller, wherein the output signal comprises data associated with physiological potentials sensed by the first electrode.

18. The method for monitoring health conditions of claim 17 further comprising:

receiving, at the computing device, labeled input data comprising physiological input data and diagnosis output data;

applying, using the computing device, a convolution neural network model to the labeled input data to generate a first set of rules associated with the physiological input data and the diagnosis output data;

applying, using the computing device, the convolution neural network model to the output signal from the microcontroller to generate a second set of rules associated with the output signal from the microcontroller; and calculating, using the computing device, a diagnosis based on a comparison of the first set of rules and the second set of rules.

19. A method of manufacturing the condition-monitoring device of claim 1 comprising:

preparing the first electrode;

preparing the stretchable circuit board;

transferring the first electrode and the stretchable circuit board to the elastomer layer; and electrically communicating the microcontroller with the stretchable circuit board and the first electrode;

wherein preparing the first electrode comprises:

coating a first silicon wafer with polydimethylsiloxane (PDMS) to create a first donor substrate;

coating the first donor substrate with a first polyimide layer;

depositing a layer of chromium;

depositing a layer of gold;

patterning an electrode design on the first donor substrate via photolithography;

coating the first donor substrate with a second polyimide layer;

etching the second polyimide layer to expose the electrode design; and removing the first electrode from the first donor substrate; and wherein preparing the stretchable circuit board comprises:

coating a second silicon wafer with PDMS to create a second donor substrate;

coating the second donor substrate with a third polyimide layer;

depositing a first layer of conductive material;

patterning a circuit design on the second donor substrate via photolithography;

coating the second donor substrate with a fourth polyimide layer;

etching the fourth polyimide layer via reactive ion etching;

depositing a second layer of conductive material;

coating the second donor substrate with a fifth polyimide layer;

exposing the circuit design by patterning the fifth polyimide layer via photolithography; and removing the stretchable circuit board from the second donor substrate.

* * * * *